(12) United States Patent
Kamatani et al.

(10) Patent No.: US 8,293,384 B2
(45) Date of Patent: Oct. 23, 2012

(54) ORGANIC COMPOUND, LIGHT-EMITTING DEVICE, AND IMAGE DISPLAY APPARATUS

(75) Inventors: Jun Kamatani, Tokyo (JP); Takayuki Horiuchi, Tokyo (JP); Naoki Yamada, Inagi (JP); Akihito Saitoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 385 days.

(21) Appl. No.: 12/763,540

(22) Filed: Apr. 20, 2010

(65) Prior Publication Data
US 2010/0270914 A1 Oct. 28, 2010

(30) Foreign Application Priority Data
Apr. 23, 2009 (JP) ................... 2009-105355

(51) Int. Cl.
H01L 51/54 (2006.01)
H01L 1/63 (2006.01)
C07C 13/465 (2006.01)
C07C 211/43 (2006.01)
C07C 25/22 (2006.01)
C07C 43/20 (2006.01)

(52) U.S. Cl. ........ 428/690; 428/917; 313/504; 313/506; 570/183; 568/633; 564/426; 585/27

(58) Field of Classification Search .................. None
See application file for complete search history.

(56) References Cited

U.S. PATENT DOCUMENTS
| | | |
|---|---|---|
| 5,130,603 A | 7/1992 | Tokailin |
| 5,858,560 A | 1/1999 | Nakamura |
| 6,093,864 A | 7/2000 | Tokailin |
| 2010/0019663 A1 | 1/2010 | Shin et al. |

FOREIGN PATENT DOCUMENTS
| | | |
|---|---|---|
| EP | 1148109 A2 | 10/2001 |
| JP | 2-247278 A | 10/1990 |
| JP | 8-113576 A | 5/1996 |
| JP | 9-241629 A | 9/1997 |
| JP | 11-012205 A | 1/1999 |
| WO | WO2010/058855 A1 | 5/2010 |

*Primary Examiner* — Dawn L. Garrett
*Assistant Examiner* — Andrew K Bohaty
(74) *Attorney, Agent, or Firm* — Canon U.S.A., Inc., IP Division

(57) ABSTRACT

An organic compound is an acenaphtho[1,2-k]benzo[e]acephenanthrene derivative represented by general formula (1):

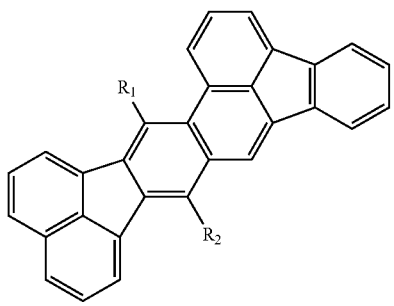

(1)

where $R_1$ and $R_2$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

5 Claims, 4 Drawing Sheets

ORGANIC COMPOUND, LIGHT-EMITTING DEVICE, AND IMAGE DISPLAY APPARATUS

BACKGROUND OF THE INVENTION

1. Field of the Invention

The present invention relates to a novel organic compound. It also relates to an organic light-emitting device and an image display apparatus that include the novel organic compound.

2. Description of the Related Art

An organic light-emitting device includes an anode, a cathode, and a thin film that contains a fluorescent organic compound and that is interposed between the anode and the cathode. When electrons and holes are injected from the respective electrodes, excitons of the fluorescent compound are generated and the light emitted by the excitons returning to their ground state is utilized by the device. Organic light-emitting devices are also called organic electroluminescence devices or organic EL devices.

Recent advancement of organic light-emitting devices has been remarkable and suggested possibilities of applying the devices to a wider range of usages. This is because they can achieve high luminance with low voltage, a wider range of emission wavelengths, rapid response, and reduction in thickness and weight.

The development of novel compounds has been actively pursued to the present. This is because creation of novel compounds is critical in making high-performance organic light-emitting devices. Japanese Patent Laid-Open Nos. 2-247278, 8-113576, and 11-12205 describe examples in which novel organic compounds are used as the materials for the emission layers.

The organic compounds and the organic light-emitting devices that contain the organic compounds described in the above-described patent citations have room for improvement from a practical viewpoint. To be more specific, optical output that achieves ever higher luminance and conversion efficiency is needed for practical application. Moreover, improvements in durability, such as in the changes over time caused by long-term use and the deterioration caused by humidity and oxygen-containing ambient gas, are needed. In order for organic light-emitting devices to be applicable to full-color displays and the like, they must achieve blue emission at high color purity and high efficiency, but this has not been satisfactorily achieved. Organic light-emitting devices that achieve high color purity, high emission efficiency, and high durability and materials that can realize such organic light-emitting devices are desired.

SUMMARY OF THE INVENTION

One aspect of the present invention provides an organic compound having an acenaphtho[1,2-k]benzo[e]acephenanthrene derivative represented by general formula (1):

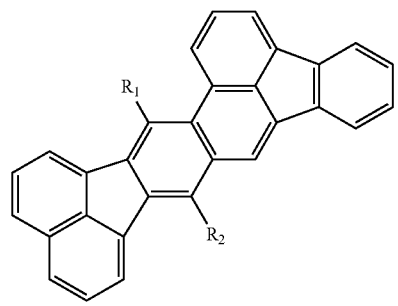

(1)

where $R_1$ and $R_2$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

Further features of the present invention will become apparent from the following description of exemplary embodiments (with reference to the attached drawings).

DESCRIPTION OF THE EMBODIMENTS

Figure 1:
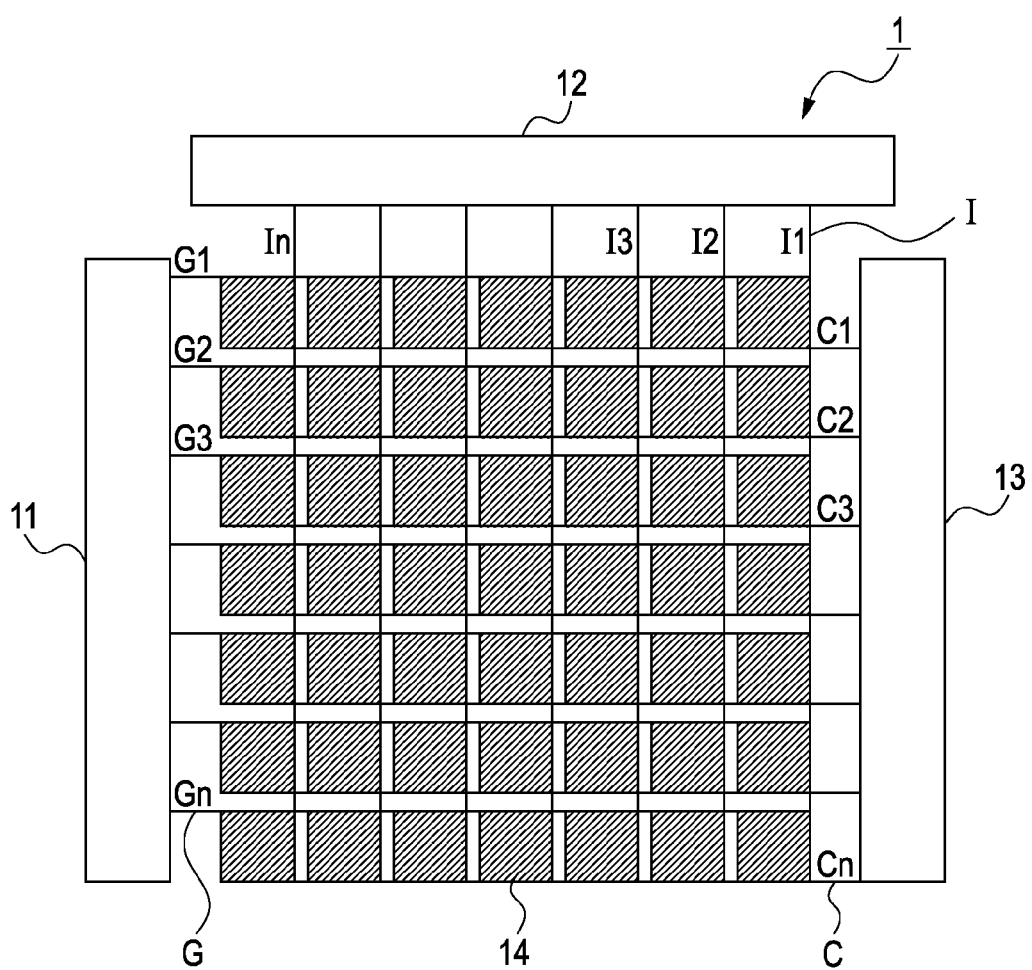
FIG. 1 is a schematic diagram illustrating an organic light-emitting device according to an aspect of the present invention and a unit configured to supply an electrical signal to the organic light-emitting device of the present invention.

A compound according to aspects of the present invention will now be described in details. The organic compound according to aspects of the present invention is an acenaphtho[1,2-k]benzo[e]acephenanthrene derivative represented by formula (1):

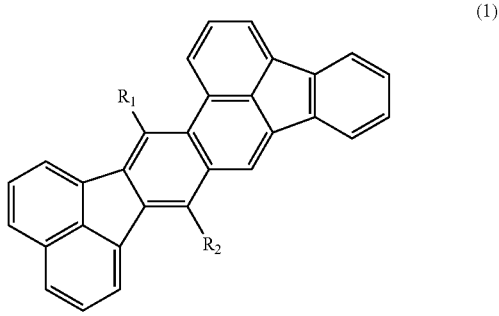

(1)

where $R_1$ and $R_2$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

In formula (1), examples of the alkyl group in the substituted or unsubstituted alkyl group include, but are not limited to, a methyl group, an ethyl group, a normal propyl group, an iso-propyl group, a normal butyl group, a tert-butyl group, a sec-butyl group, an octyl group, a 1-adamantyl group, and a 2-adamantyl group.

In formula (1), examples of the alkoxy group in the substituted or unsubstituted alkoxy group include, but are not limited to, a methoxy group, an ethoxy group, a propoxy group, 2-ethyl-octyloxy group, a phenoxy group, 4-tert-butylphenoxy group, a benzyloxy group, and a thienyloxy group.

In formula (1), examples of the amino group in the substituted or unsubstituted amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

In formula (1), examples of the aryl group in the substituted or unsubstituted aryl group include, but are not limited to, a phenyl group, a naphthyl group, an indenyl group, a biphenyl group, a terphenyl group, and a fluorenyl group.

In formula (1), examples of the heterocyclic group in the substituted or unsubstituted heterocyclic group include, but are not limited to, a pyridyl group, an oxazolyl group, an oxadiazolyl group, a thiazolyl group, a thiadiazolyl group, a carbazolyl group, an acridinyl group, and a phenanthrolyl group.

In formula (1), examples of the substituents that may be included in the above-described substituents, namely, the alkyl, alkoxy, amino, aryl, and heterocyclic groups represented by $R_1$ or $R_2$, include, but are not limited to, alkyl groups such as a methyl group, an ethyl group, and a propyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, a propoxyl group, and a phenoxyl group; a cyano group; and halogen atoms such as fluorine, chlorine, bromine, and iodine atoms.

Specific examples of the compound represented by general formula (1) are as follows. These examples do not limit the scope of the present invention.

A1

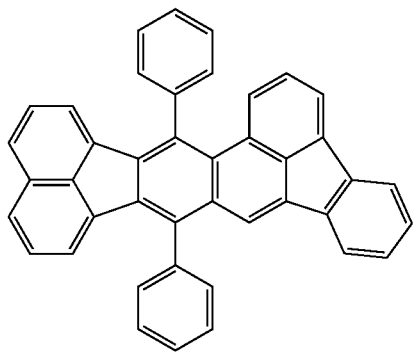

A2

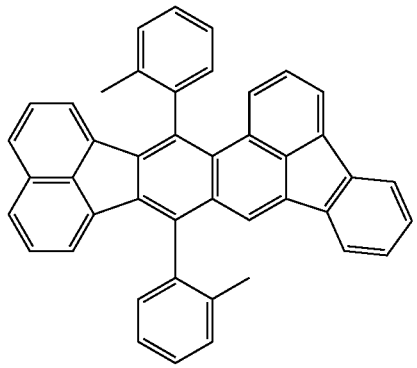

-continued

A3

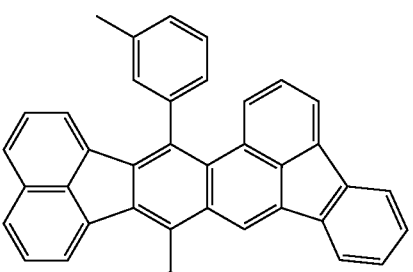

A4

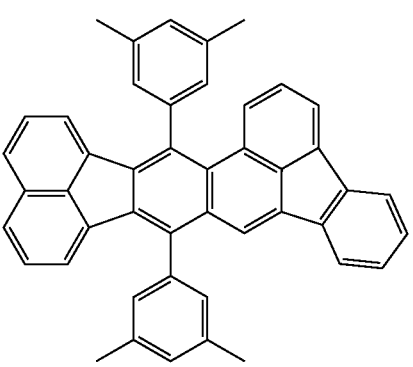

A5

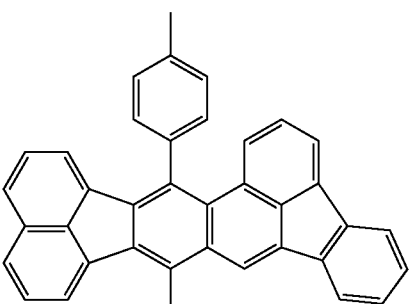

A6

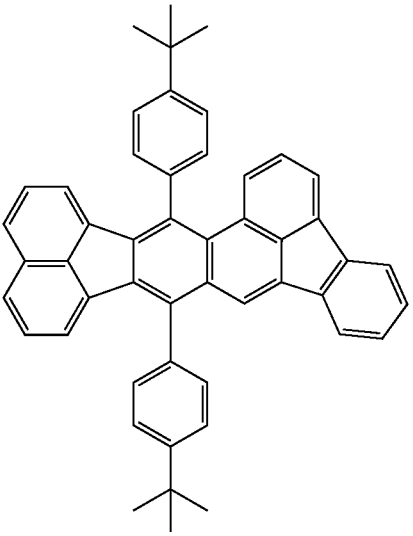

A7
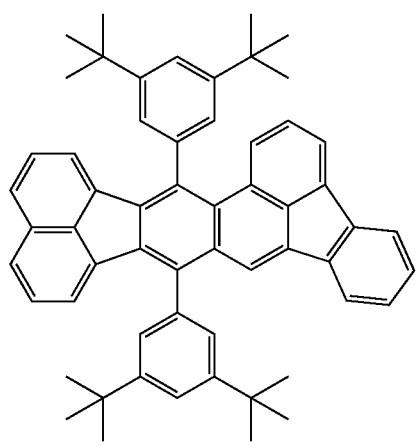
A8
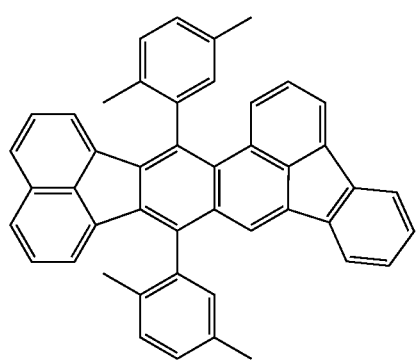
A9
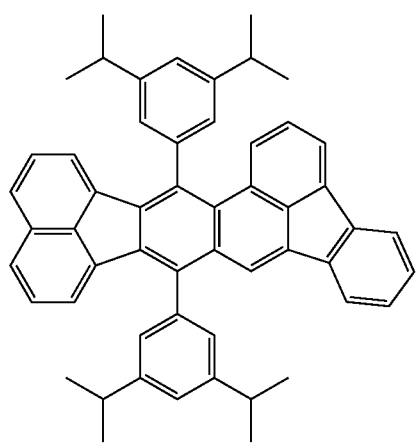
A10
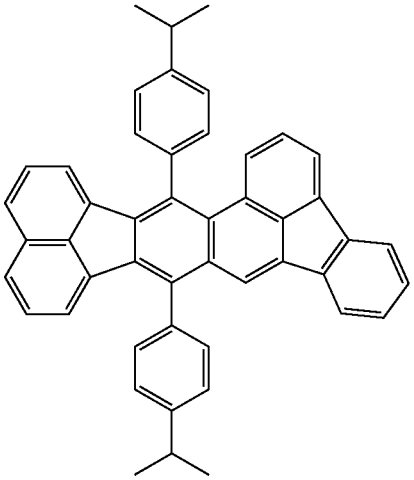
A11
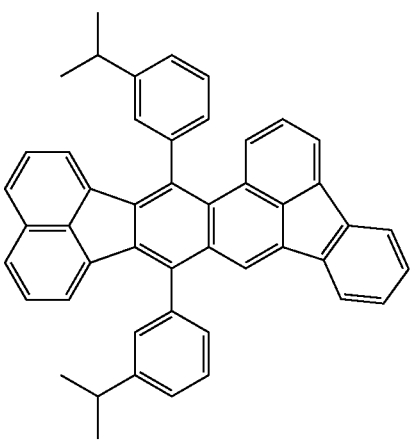
A12
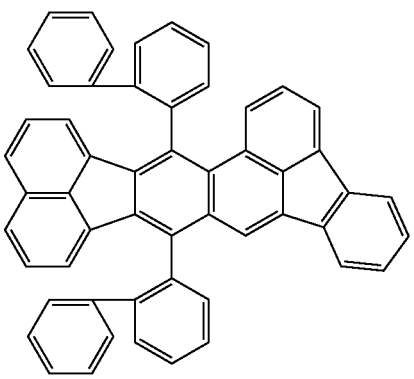

A13
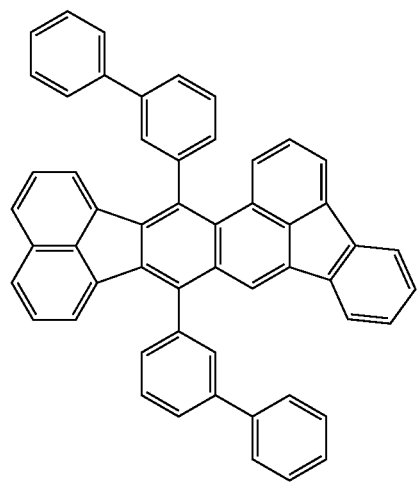
A14
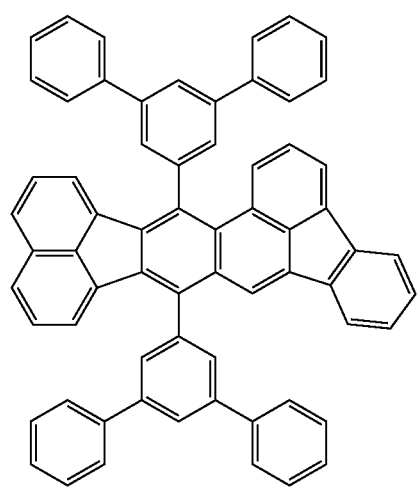
A15
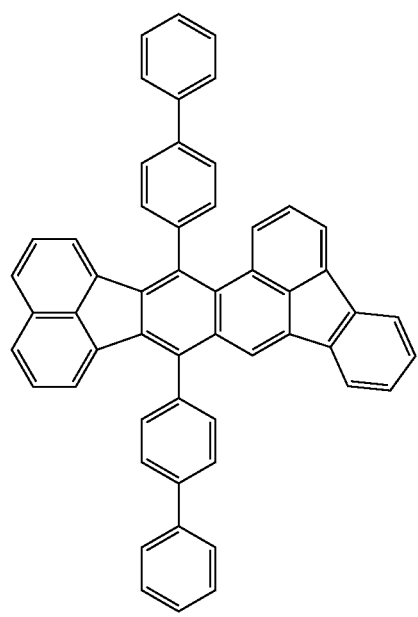
A16
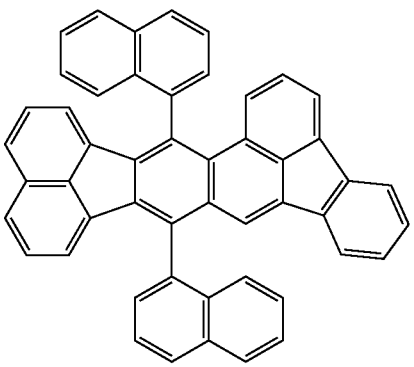
A17
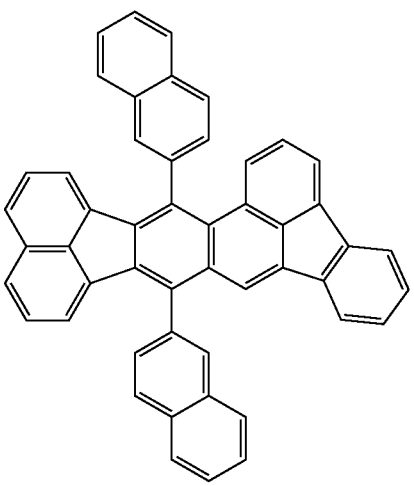
A18
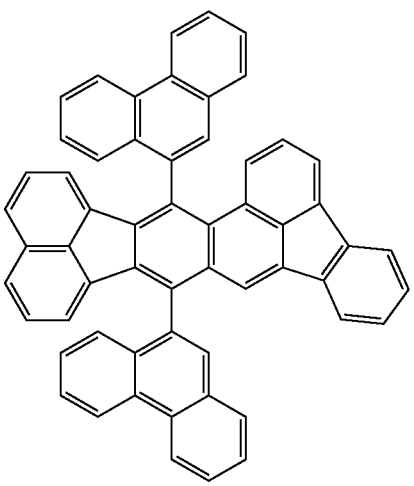

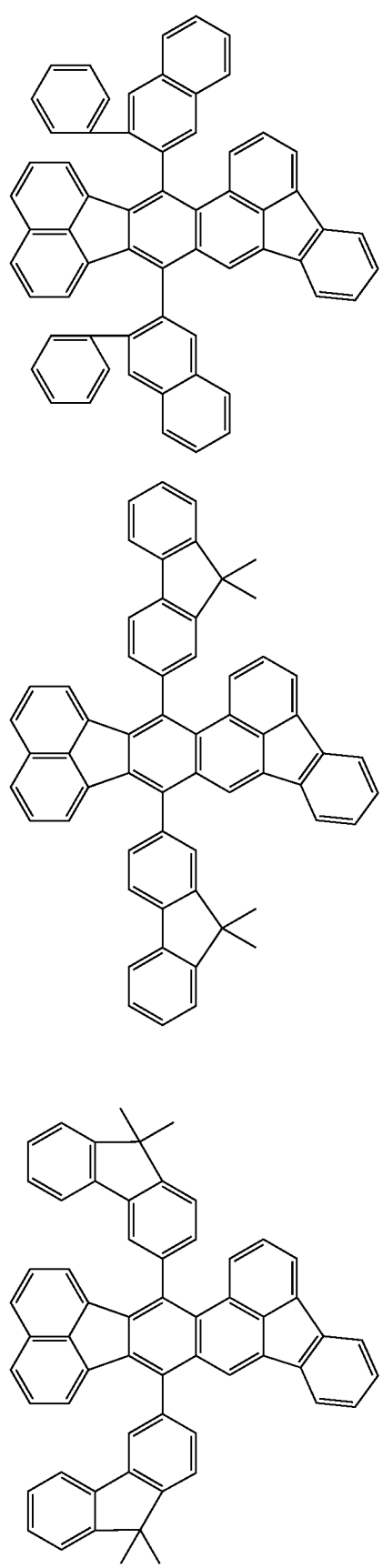
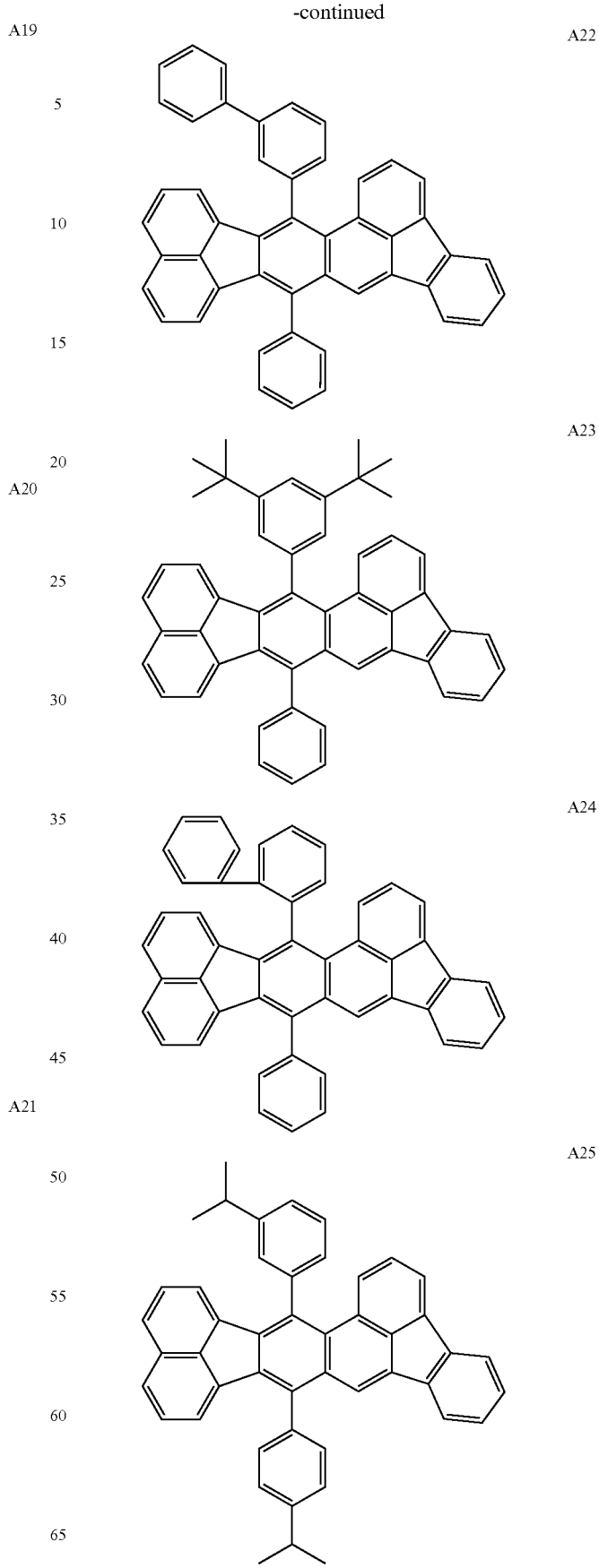

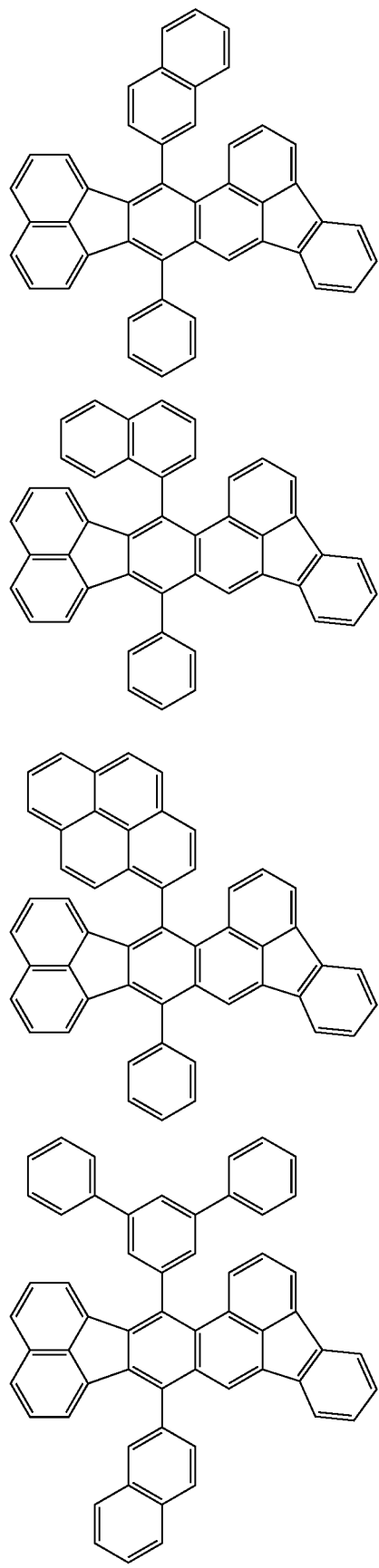
A26
A27
A28
A29
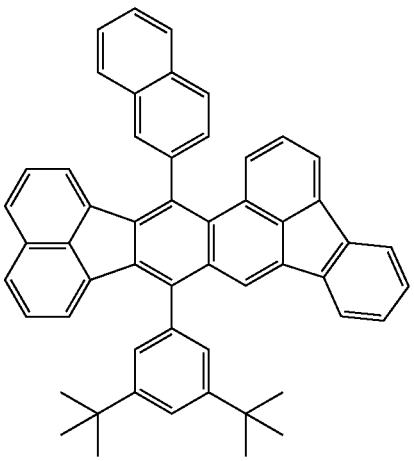
A30
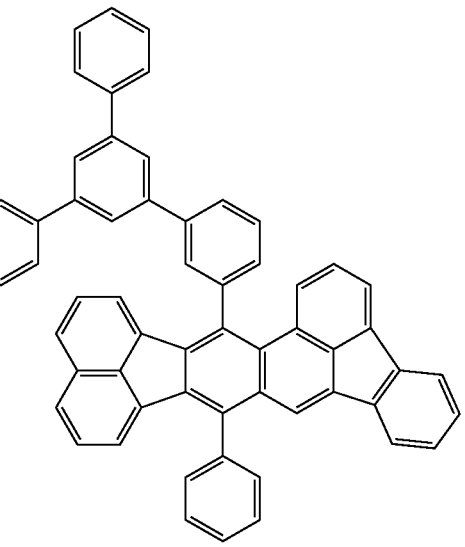
A31
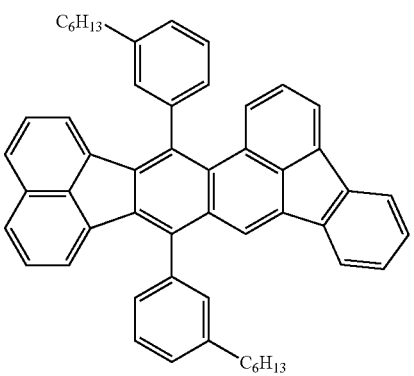
A32

A33
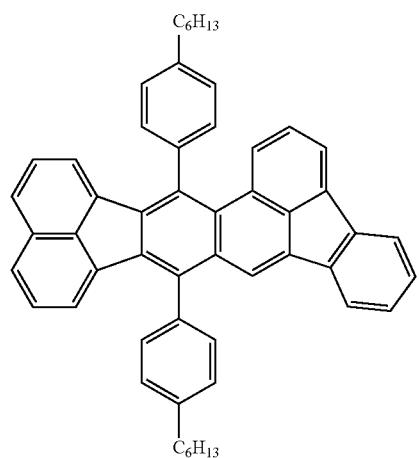
A34
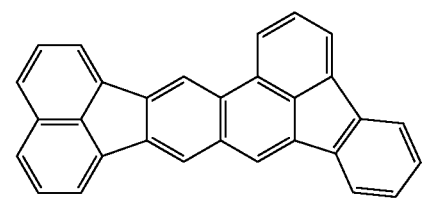
B1
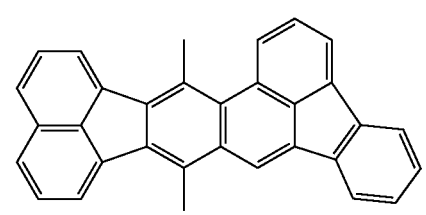
B2
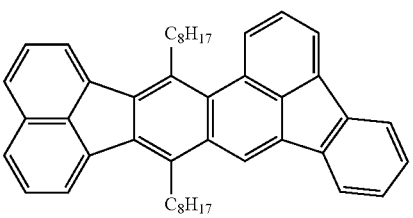
B3
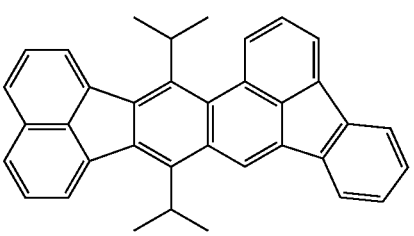
B4
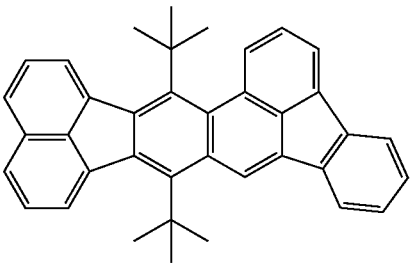
B5
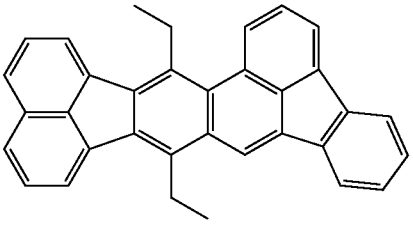
B6
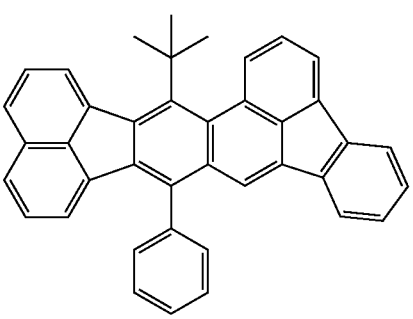
B7
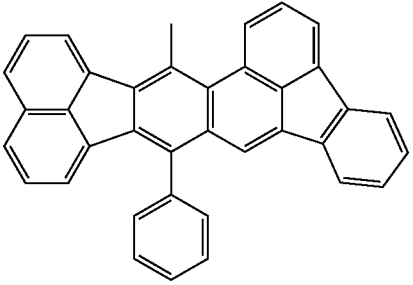
B8

-continued
B9
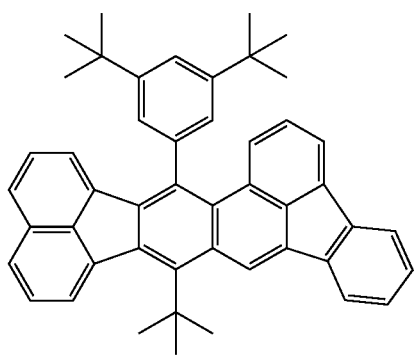
B10
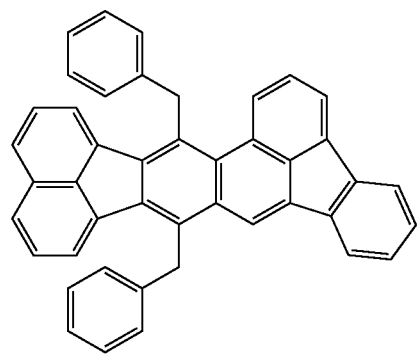
B11
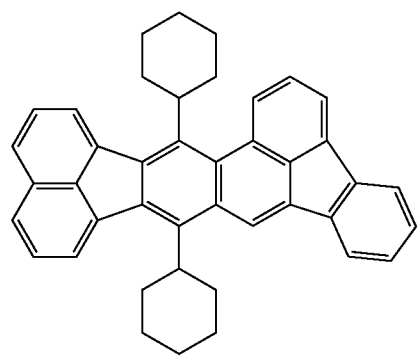
B12
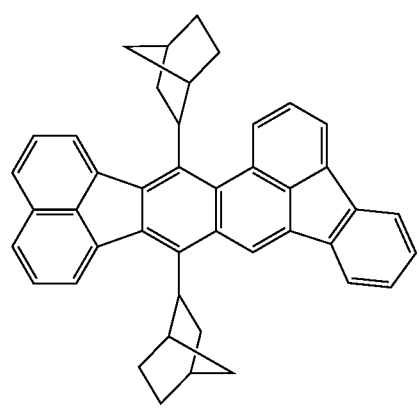
B13
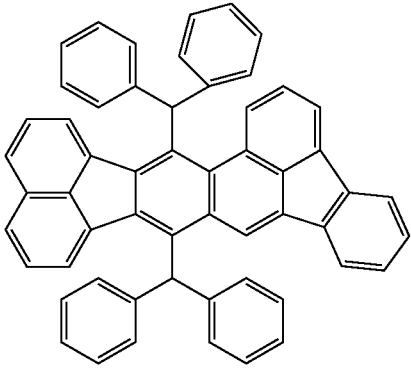
C1
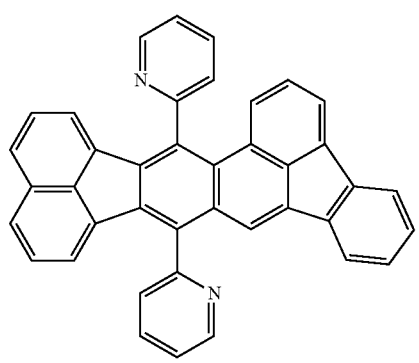
C2
C3

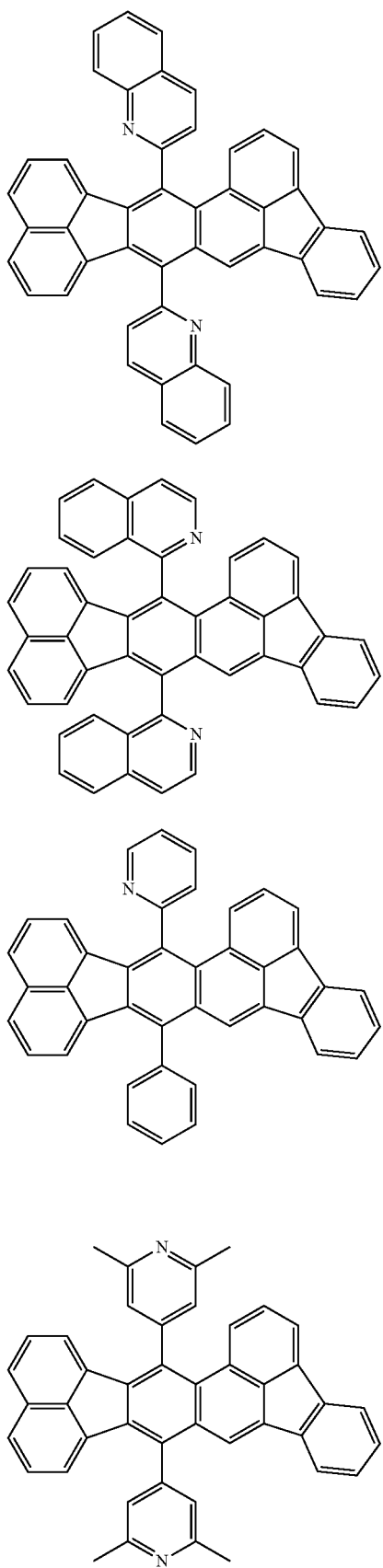
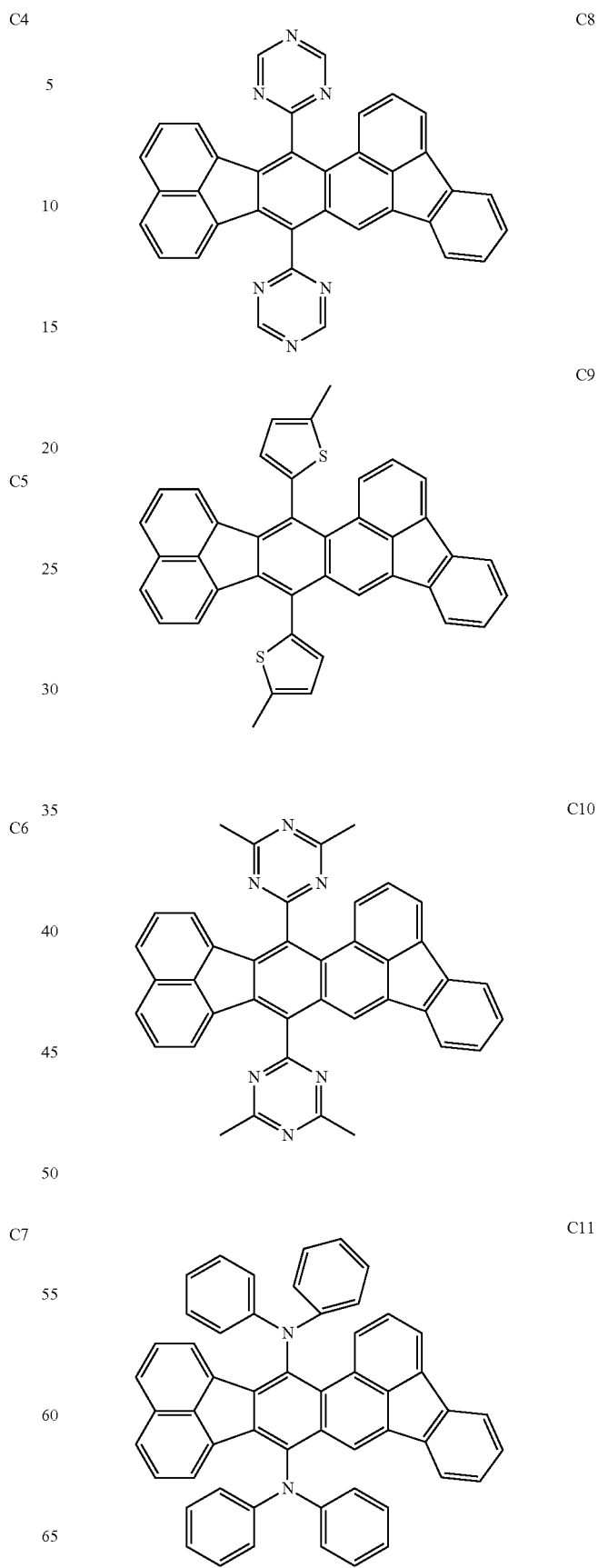

-continued
C12
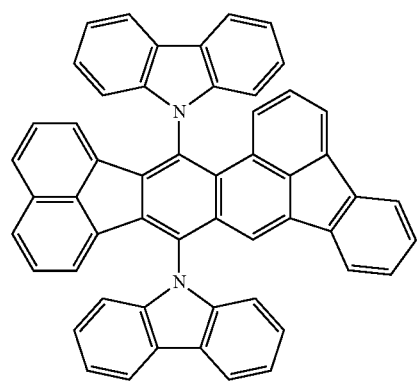
C13
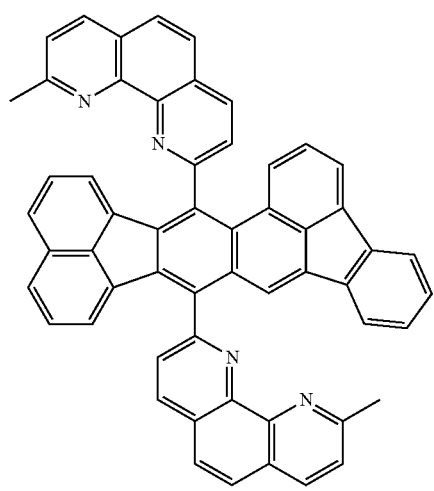
C14
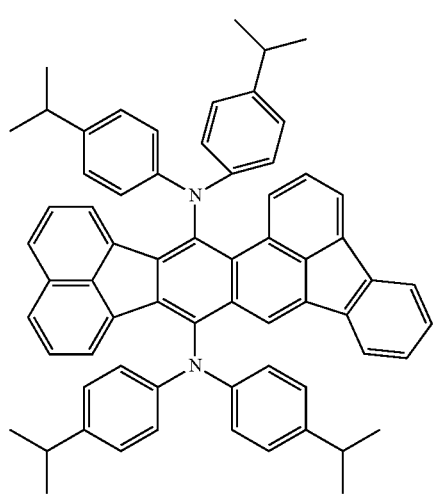
-continued
C15
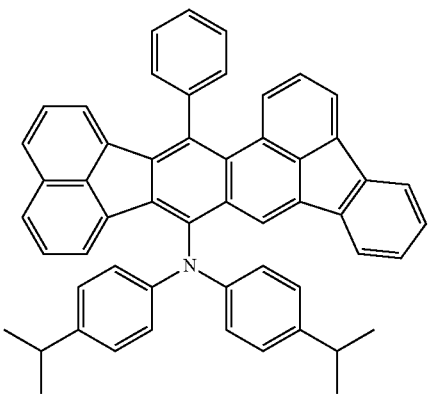
C16
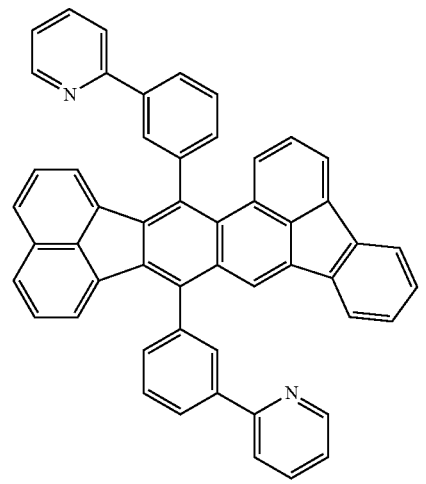
C17
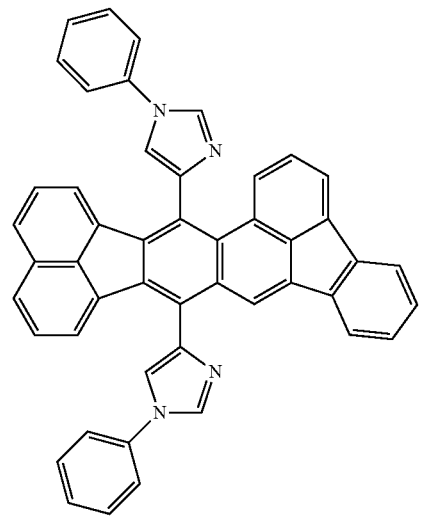

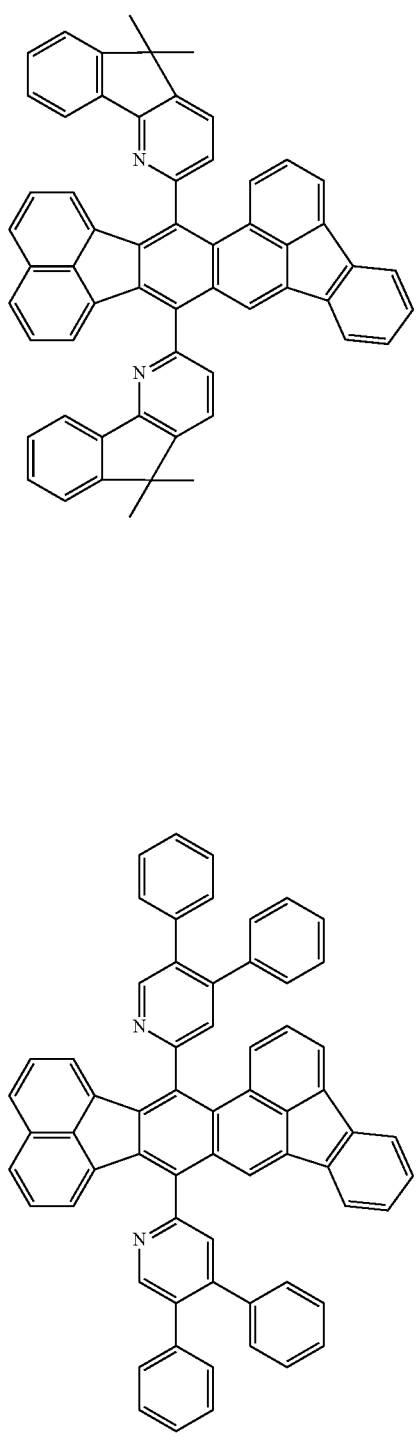

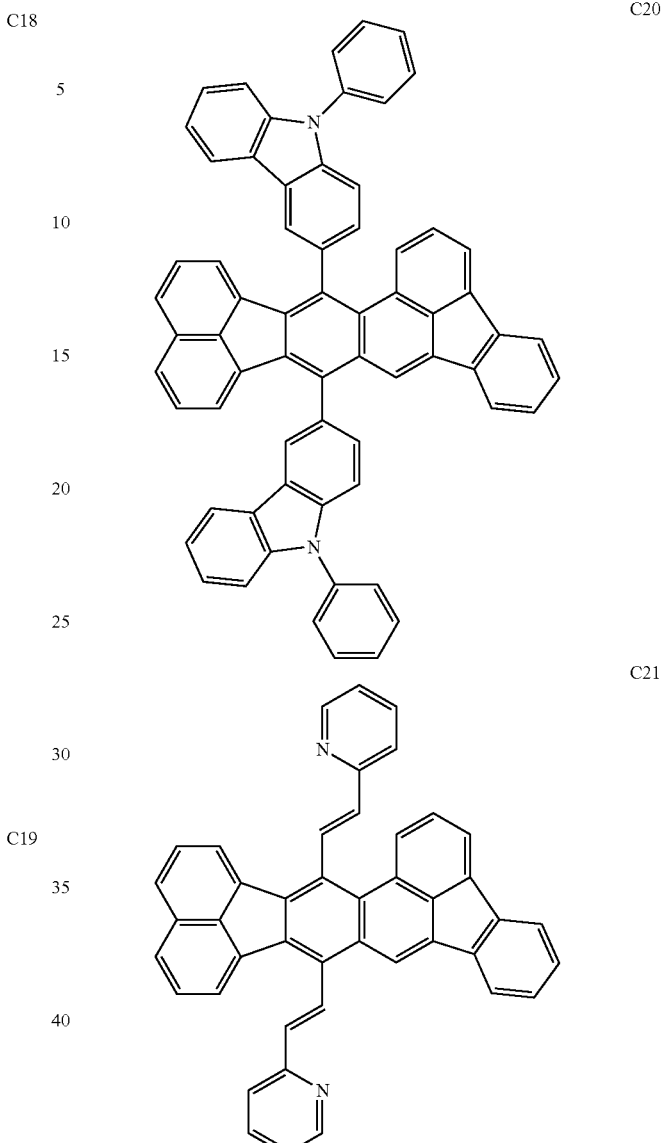

The novel organic compound according to aspects of the present invention will now be described in further detail.

In general, in order to increase the emission efficiency of organic light-emitting devices, the emission quantum yield of the emission center material itself is desirably relatively high.

This requires, first, that the oscillator strength be relatively high and, second, that the oscillating portion of the backbone associated with emission be relatively small.

An physical property that may be important for a material suited to emit blue light in organic EL displays is that the emission peak of the light-emitting material is in the range of 430 to 480 nm. Some of the organic compounds according to aspects of the present invention are capable of emitting light having an emission peak in the range of 430 to 480 nm.

With respect to the first condition, it may be important to enhance symmetry of the backbone associated with emission from molecules. However, no emission would occur under a forbidden transition condition peculiar to highly symmetrical molecules. When the conjugation is extended along the axis which is the direction in which the plane of conjugation is the longest, the dipole moment of the molecule increases and the oscillator strength improves.

The organic compounds according to aspects of the present invention include fused ring structures formed by extending the conjugation from the 8-position to the 11-position of benzo[k]fluoranthene. Such structures further increase the moment relative to the benzo[k]fluoranthene. Thus, the organic compound according to aspects of the present invention structurally has a relatively high oscillator strength. With respect to the second condition, the decrease in quantum yield resulting from vibrations caused by rotation can be suppressed when the backbone associated with emission is free of any rotational structure.

The basic skeleton of the organic compounds according to aspects of the present invention, i.e., the acenaphtho[1,2-k]benzo[e]acephenanthrene backbone, itself has a maximum emission wavelength in the blue region. Moreover, this basic skeleton has little or no rotational structure and therefore can suppress the decrease in quantum yield caused by rotation oscillation.

A comparative example of the basic skeleton is benzo[k]fluoranthene. When 7,12-diphenylbenzo[k]fluoranthene having phenyl groups substituting the 7- and 12-positions of benzo[k]fluoranthene is compared with 9,16-diphenylacenaphtho[1,2-k]benzo[e]acephenanthrene having phenyl groups substituting the 9- and 16-positions of acenaphtho[1,2-k]benzo[e]acephenanthrene according to aspects of the present invention, the maximum wavelength of the former is 428 nm whereas the maximum wavelength of the latter is 440 nm.

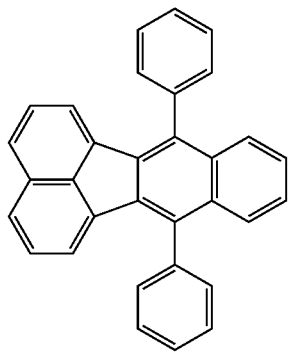

7,12-Diphenylbenzo[k]fluoranthene

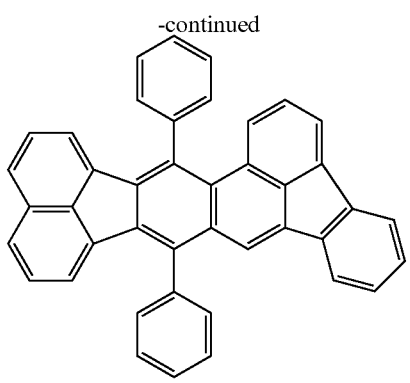

9,16-Diphenylacenaphtho[1,2-k]benzo[e]acephenanthrene

The organic compound according to aspects of the present invention can emit light close to blue because it has this basic skeleton. Thus, in tuning the color of emission by introduction of substituents or the like, i.e., in optimizing the material so that the material can emit desired blue light, the color of emission can be tuned by introducing fewer substituents than in the case of using compounds having a benzo[k]fluoranthene backbone. This also leads to reduction of vibrational deactivation caused by substituents and is effective for enhancing the efficiency and extending the lifetime of the light-emitting device.

Accordingly, the organic compound according to aspects of the present invention is suited to emit blue light and may achieve a high quantum yield owing to the basic skeleton.

The organic compound according to aspects of the present invention also has low HOMO-LUMO energy levels since two five-membered-ring structures are included in the backbone. A low oxidation potential means that a large amount of energy is required for oxidation. In other words, the organic compound according to aspects of the present invention is stable against oxidation. The organic compound is also suited as an electron-trapping light-emitting material when it is used as a light-emitting material.

The organic compound according to aspects of this invention may be highly planar and may easily generate excimers by intermolecular stacking when it is unsubstituted. Thus, in order to suppress generation of excimers, substituents such as an aryl group, an alkyl group, an amino group, etc., may be introduced to the 9- and 16-positions of the organic compound.

The dihedral angle of the bond between the acenaphtho[1,2-k]benzo[e]acephenanthrene backbone and the aryl group was calculated. Calculation was done by quantum chemical calculation at the B3LYP/6-31G* level using a density functional theory.

The results are shown in Table 1.

TABLE 1

| | Structural formula | Dihedral angle |
|---|---|---|
| Phenyl substitution at 1-position | | 68.8° |

TABLE 1-continued

| | Structural formula | Dihedral angle |
|---|---|---|
| Phenyl substitution at 4-position | | 57.2° |
| Phenyl substitution at 6-position | | 37.8° |
| Phenyl substitution at 9-position | | 89.3° |
| Phenyl substitution at 11-position | | 39.7° |

TABLE 1-continued

| | Structural formula | Dihedral angle |
|---|---|---|
| Phenyl substitution at 12-position | 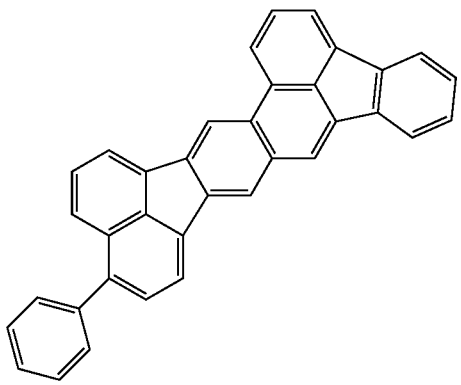 | 49.9° |
| Phenyl substitution at 16-position | 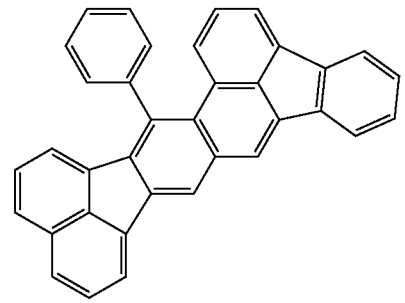 | 88.3° |

According to these results, in the acenaphtho[1,2-k]benzo[e]acephenanthrene, i.e., the basic skeleton, the substitution positions most effectively suppressing generation of the excimers by the intermolecular stacking are the 9- and 16-positions where the dihedral angles are large. When these positions are substituted with phenyl groups, the dihedral angle will be 88° or more, i.e., substantially perpendicular with respect to the plane of the basic skeleton. This shows that these positions can be used to suppress generation of excimers. As to the increase in wavelength due to spreading of the electron cloud, the conjugation does not easily spread to the substituents due to this substantially perpendicular arrangement. Thus, it is clear that these positions of substituents help maintain the electronic state of the basic skeleton. Here, "perpendicular" means that the plane of each phenyl group is perpendicular to the plane of acenaphtho[1,2-k]benzo[e]acephenanthrene.

Due to this arrangement, in the case of fused rings in which the substituents are phenyl groups and/or hydrocarbons among the aryl groups as in A1 to A34, since the substituents are perpendicular to the basic skeleton, the structure of the compound becomes three dimensional, stacking of molecules can be suppressed, and the concentration quenching can be suppressed. Since hydrocarbons are used as the substituents, an oxidation-reduction potential not much different from that of the basic skeleton can be maintained. Moreover, because of the perpendicular arrangement, further introduction of a substituent group into the aryl group contributes little to increasing the wavelength. To be more specific, such an introduction will only increase the wavelength by about several to 20 nanometers.

When the substituents are alkyl groups as in B2 to B13, generation of excimers can be suppressed. In addition, when the unsubstituted compound constituted by only the basic skeleton and the substituted compounds are compared, there is substantially no difference in the maximum emission wavelength. This is because conjugation does not occur between the basic skeleton and the substituents. In other words, the substituents are cut away from the basic skeleton in terms of conjugation. As for the oxidation-reduction potential, the oxidation potential tends to be high because of the electron-donating property and the stability tends to be low. However, when fused structures are introduced to the ends of alkyl groups, generation of excimers can be controlled.

In the case where the substituents have aryl groups including hetero structures or substituents containing hetero atoms such as amino groups as in C1 to C21, the change in oxidation-reduction potential derived from the hetero structure can be controlled. As a result, the maximum emission wavelength can be increased and the organic compound can be used not only as electron-trapping light-emitting materials but also as electron-transporting light-emitting materials, hole-transporting light-emitting materials, and hole-trapping light-emitting materials. However, compared to the cases in which the substituted positions are other than 9- and 16-positions, the effect is small.

As described above, the organic compounds according to aspects of this invention which are acenaphtho[1,2-k]benzo[e]acephenanthrene derivatives can be used in the blue region because of their basic skeletons and can achieve a high quantum yield.

At least one acenaphtho[1,2-k]benzo[e]acephenanthrene derivative is contained in an organic compound layer of an organic light-emitting device according to aspects of the present invention. The compound of acenaphtho[1,2-k]benzo[e]acephenanthrene according to aspects of this invention can be used as a light-emitting material for a blue light-emitting device, but the usage is not limited to this. To be more specific, the acenaphtho[1,2-k]benzo[e]acephenanthrene derivative according to aspects of this invention can be used as a light-emitting material, a host material, a transport material, or the like, of a green light-emitting device.

The organic compound represented by general formula (1) can be synthesized through synthetic route 1 described below. As for the substituent, various types of substituents are introduced. For example, synthesis can be conducted by substituting hydrogen atoms with other substituents, such as an alkyl group, a halogen atom, and a phenyl group.

Synthetic route 1:

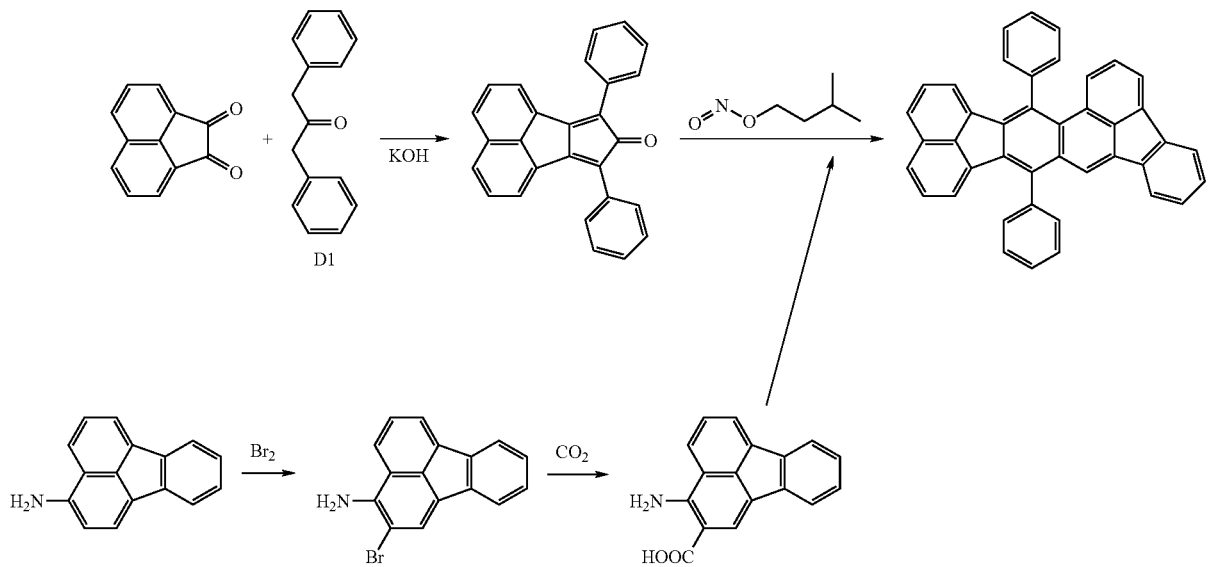

Various organic compounds can be synthesized by using various different compounds as starting material D1. The table below shows example of the organic compounds obtained by the synthesis (Synthetic Compounds in Table 2 below). Table 2 also indicates starting materials D1 of these compounds.

TABLE 2

| | D1 | Synthetic Compound |
|---|---|---|
| Synthetic Example 1 | | |
| Synthetic Example 2 | | |

| | D1 | Synthetic Compound |
|---|---|---|
| Synthetic Example 3 | 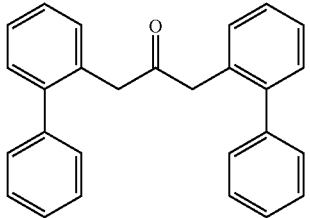 | 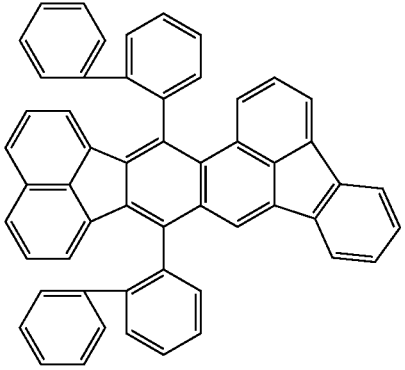 |
| Synthetic Example 4 | 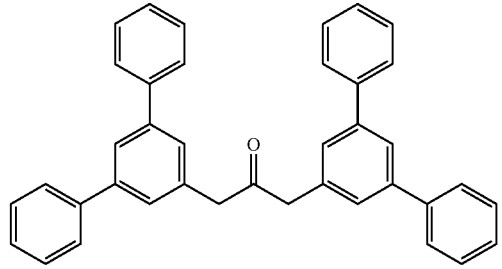 | 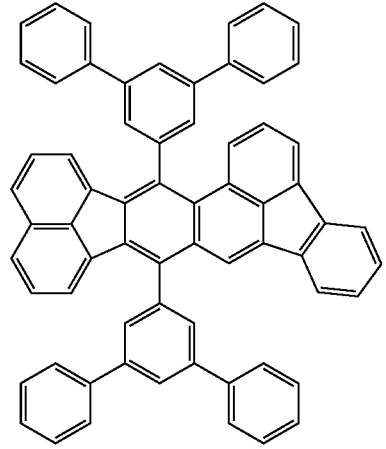 |
| Synthetic Example 5 | 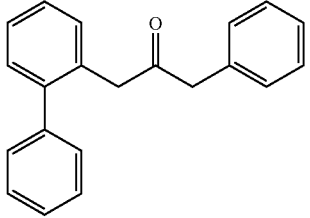 | 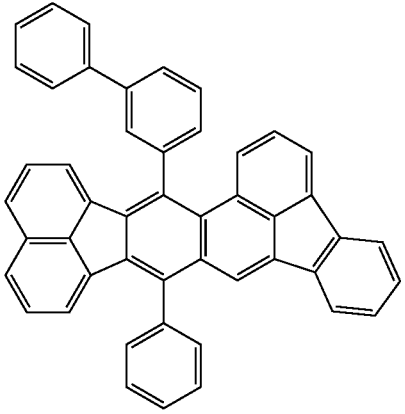 |

TABLE 2-continued

| | D1 | Synthetic Compound |
|---|---|---|
| Synthetic Example 6 | | |
| Synthetic Example 7 | | |
| Synthetic Example 8 | | |

US 8,293,384 B2
35 36
TABLE 2-continued
| D1 | Synthetic Compound |
|---|---|
| Synthetic Example 9 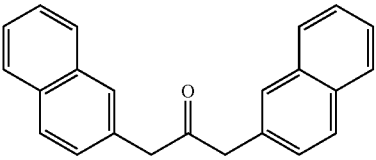 | 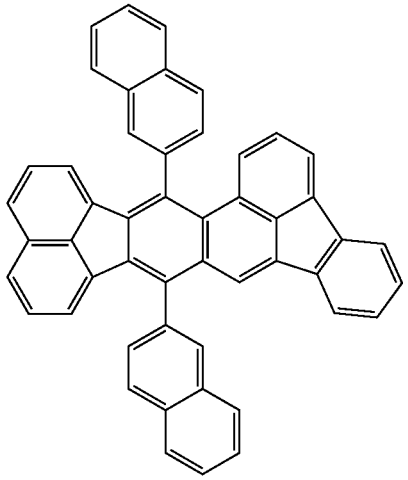 |
| Synthetic Example 10 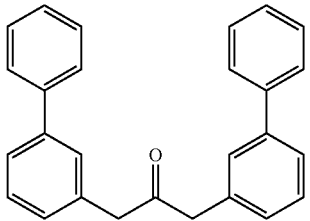 | 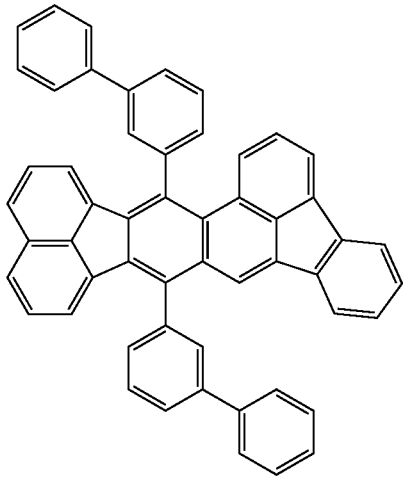 |
| Synthetic Example 11 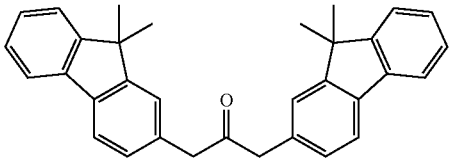 | 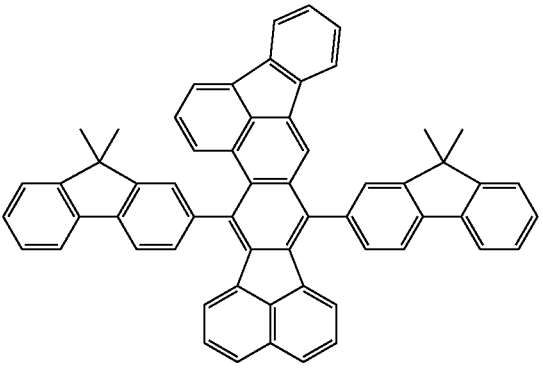 |

TABLE 2-continued
| | D1 | Synthetic Compound |
|---|---|---|
| Synthetic Example 12 | 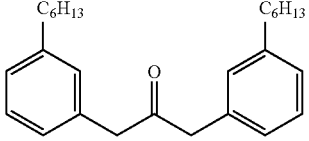 | 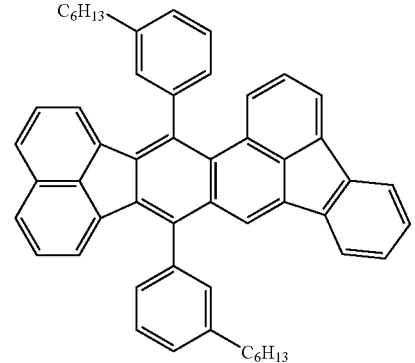 |
| Synthetic Example 13 | 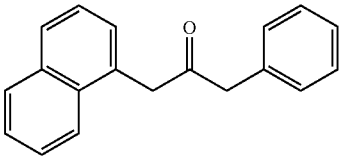 | 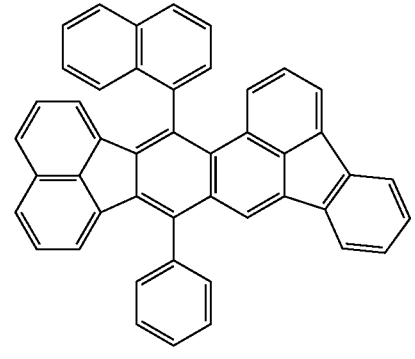 |
| Synthetic Example 14 | 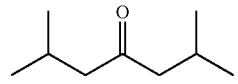 | 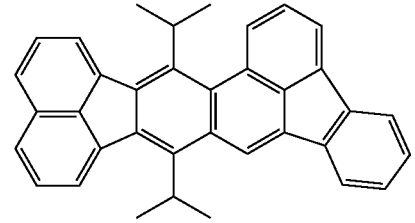 |
| Synthetic Example 15 | 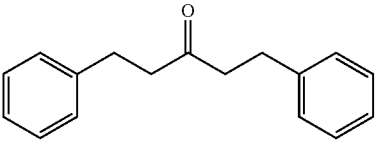 | 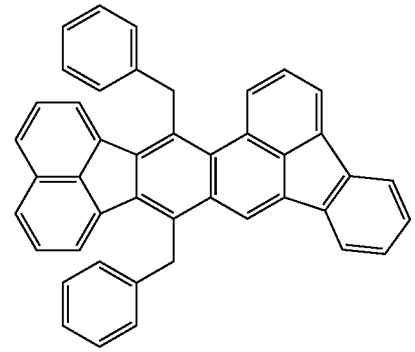 |

TABLE 2-continued

| D1 | Synthetic Compound |
|---|---|
| Synthetic Example 16 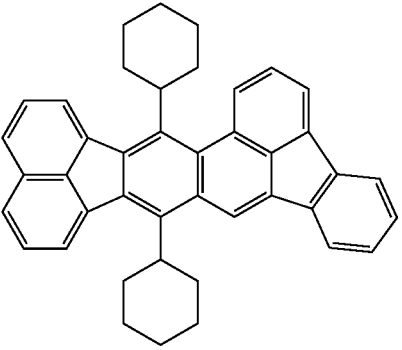 | |
| Synthetic Example 17 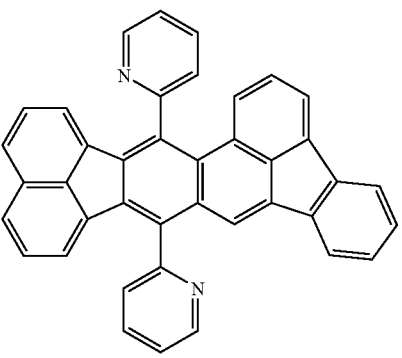 | |

Next, the organic light-emitting device according to aspects of the present invention is described.

The organic light-emitting device according to aspects of this invention at least includes a pair of electrodes, i.e., an anode and a cathode, and an organic compound layer interposed between the electrodes. This organic compound layer contains the organic compound represented by general formula (1) above. In the organic light-emitting device, the organic compound interposed between the electrodes functions as a light-emitting material and emits light.

In the case where a plurality of organic compound layers are provided and one of them is an emission layer, the emission layer may be entirely or partly composed of the organic compound according to aspects of the present invention.

When the emission layer is partly composed of the organic compound according to aspects of the present invention, the organic compound according to aspects of the present invention may be the main component or a minor component of the emission layer.

The "main component" is, for example, a component with a large content in terms of weight or moles among all compounds constituting the emission layer. The "minor component" is the component with a small content.

The material that serves as the main component can also be called a "host material". The material that serves as a minor component can be called "dopant (guest) material", "emitting assist material", or "charge injection material".

When the organic compound according to aspects of the present invention is used as a guest material, the guest material concentration relative to the host material is preferably 0.01 to 20 wt % and more preferably 0.5 to 10 wt %. The wavelength of the light emitted from the emission layer can be made longer than the wavelength of the solution by 5 nm to 20 nm by adjusting the concentration of the guest material in any one of these two ranges.

When the emission layer contains a host material and a guest material having a carrier transport property, the process that leads to emission includes following steps:
1. Transportation of electrons and holes inside the emission layer.
2. Generation of excitons of the host material.
3. Transfer of excitation energy among molecules of the host material.
4. Transfer of excitation energy from the host material to the guest material.

The energy transfer in the respective steps and the emission occur in competition with various deactivation processes.

Naturally, in order to enhance the emission efficiency of the organic light-emitting device, the emission quantum yield of the emission center material (e.g., guest material) itself must be high. However, one major challenge is how to efficiently transfer energy between the molecules of the host material and between the host material and the guest material. Although the exact cause of emission deterioration by electrical current is not yet clear, the inventors believe that the emission center material or the environmental changes brought to the emission center material by the nearby molecules may be attributable to the deterioration.

The inventors of the present invention have conducted various investigations and found that when a compound represented by general formula (1) according to aspects of the present invention described above is used as the host or guest material or, in particular, as the guest material in the emission layer, the device outputs light highly efficiently at a high luminance and has considerably high durability.

The organic light-emitting device according to aspects of this invention will now be described in detail.

The organic light-emitting device at least includes a pair of electrodes, i.e., an anode and a cathode, and an organic compound layer interposed between the electrodes. The organic compound layer contains at least one organic compound represented by general formula (1).

One or more compound layers other than the organic compound layer may be provided between the pair of electrodes. In other words, two or more compound layers including the organic compound layer described above may be provided between the pair of electrodes. In such a case, the organic light-emitting device is called a multilayer organic light-emitting device.

First to fifth examples of multilayer organic light-emitting devices are described below.

A first example of a multilayer organic light-emitting device is a structure in which an anode, an emission layer, and a cathode are sequentially layered on a substrate. This type of organic light-emitting device may be useful when a material having all of the hole transport property, the electron transport property, and the emission property by itself is used in the emission layer, or when compounds having respective properties are mixed and used in the emission layer.

A second example of a multilayer organic light-emitting device is a structure in which an anode, a hole transport layer, an electron transport layer, and a cathode are sequentially layered on a substrate. This type of organic light-emitting device may be useful when a material having a hole transport property and a material having an electron transport property are respectively used in corresponding layers, or when a material having both these properties is used in both layers in combination with a simple hole transport or electron transport substance that has no light-emitting property. In such a case, the emission layer is either the hole transport layer or the electron transport layer.

A third example of a multilayer organic light-emitting device is a structure in which an anode, a hole transport layer, an emission layer, an electron transport layer, and a cathode are sequentially layered on a substrate. In this structure, the carrier transport function and the light-emitting function are separated. Compounds respectively having a hole transport property, an electron transport property, and a light-emitting property may be adequately combined and used in the device. This significantly increases the flexibility of choices of materials. Moreover, since various different compounds with different emission wavelengths can be used, the variety of the emission hue can be widened. Carriers or excitons can be effectively confined in the center emission layer to enhance the emission efficiency.

A fourth example of a multilayer organic light-emitting device is a structure in which an anode, a hole injection layer, a hole transport layer, an emission layer, an electron transport layer, and a cathode are sequentially layered on a substrate. This structure improves the adhesiveness between the anode and the hole transport layer and improves the hole injectability, which is effective for decreasing the voltage.

A fifth example of a multilayer organic light-emitting device is a structure in which an anode, a hole transport layer, an emission layer, a hole/exciton-blocking layer, an electron transport layer, and a cathode are sequentially layered on a substrate. In this structure, a layer (hole/exciton-blocking layer) that prevents holes or excitons from reaching the cathode is interposed between the emission layer and the electron transport layer. Since a compound having a significantly high ionization potential is used in the hole/exciton-blocking layer, the emission efficiency can be effectively enhanced.

According to aspects of the present invention, an emission region containing a compound represented by general formula (1) refers to a region of the emission layer described above.

The multilayer structures of the first to fifth examples are only basic device structures and do not limit the structure of the organic light-emitting device that uses the compound according to aspects of the present invention. For example, various other layer structures can also be employed, such as providing an insulating layer at the interface between an electrode and an organic layer, providing an adhesive layer or an interference layer, and designing the electron or hole transport layer to be made up of two layers with different ionization potentials.

The compound represented by general formula (1) used according to aspects of the present invention may be used in any one of the first to fifth examples described above.

In the organic light-emitting device according to aspects of this invention, at least one organic compound represented by general formula (1) can be contained in the organic compound-containing layer. In particular, at least one organic compound represented by general formula (1) may be used as the guest material in the emission layer. Alternatively, the organic compound according to aspects of the present invention may be used as the host material in the emission layer.

The organic compound according to aspects of the present invention may be used in any layers other than the emission layer such as a hole injection layer, a hole transport layer, a hole/exciton-blocking layer, an electron transport layer, and electron injection layer.

In addition to the organic compound according to aspects of the present invention, existing low-molecular-weight and polymer hole transport compounds, light-emitting compounds, and electron transport compounds and the like may be used in combination if needed.

Examples of such compounds are as follows.

Hole injection/transport materials may have a high hole mobility so that holes can be easily injected from the anode and the injected holes can be transferred to the emission layer. Examples of the low-molecular-weight and polymer materials having hole injection/transport functions include, but are not limited to, triarylamine derivatives, phenylenediamine derivatives, stilbene derivatives, phthalocyanine derivatives, porphyrin derivatives, poly(vinyl carbazole), polythiophene, and other conductive polymers.

Examples of the host material include, but are not limited to, the compounds indicated in Table 3 and derivatives thereof; fused-ring compounds such as fluorene derivatives, naphthalene derivatives, anthracene derivatives, pyrene derivatives, carbazole derivatives, quinoxaline derivatives, and quinoline derivatives; organoaluminum complexes such as tris(8-quinolinolato)aluminum; organozinc complexes; and polymer derivatives such as triphenylamine derivatives, polyfluorene derivatives, and polyphenylene derivatives.

TABLE 3
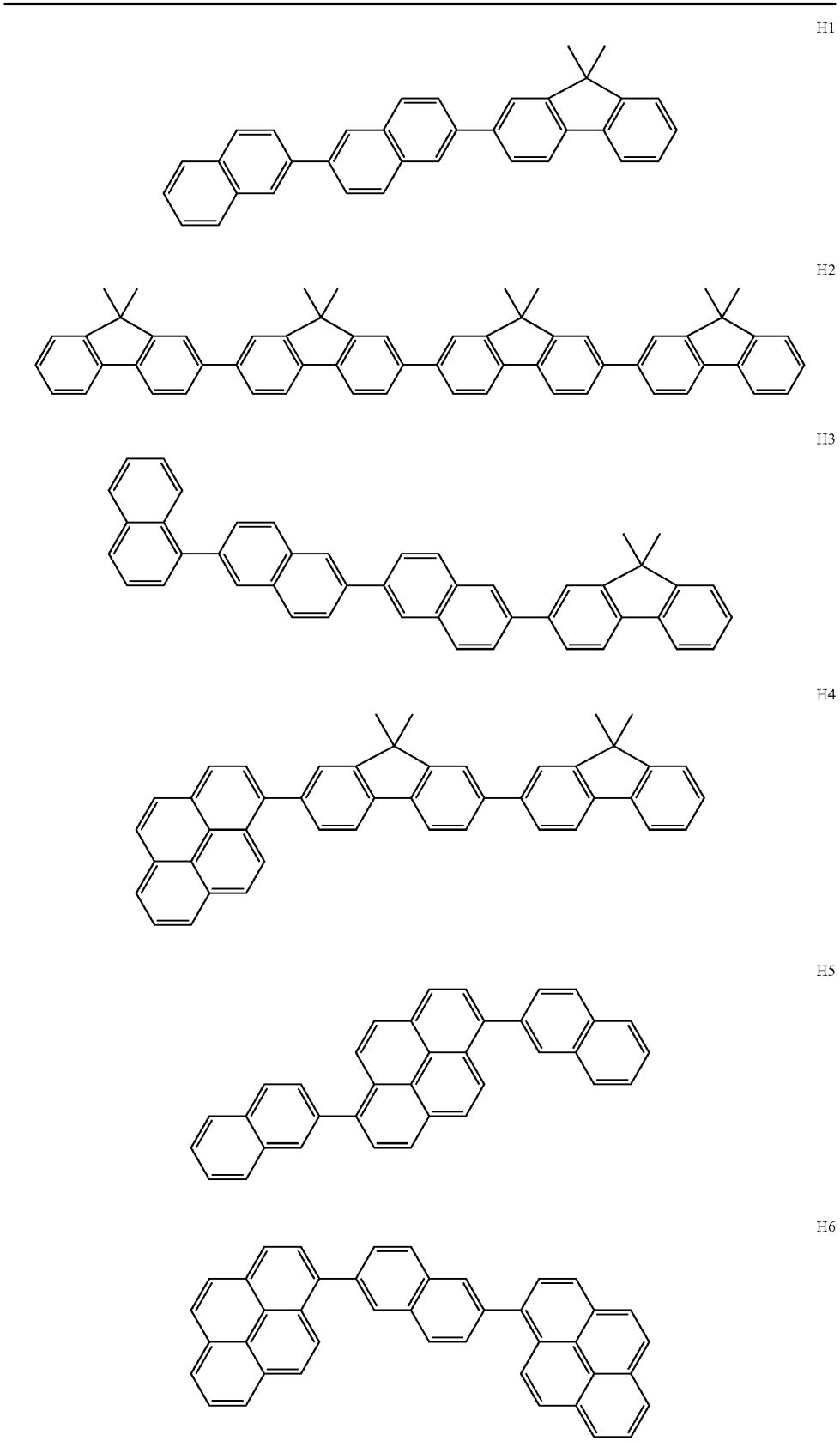

TABLE 3-continued
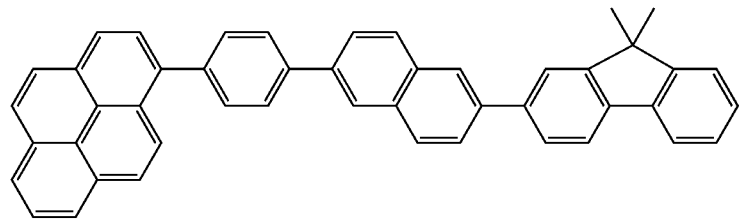
H7
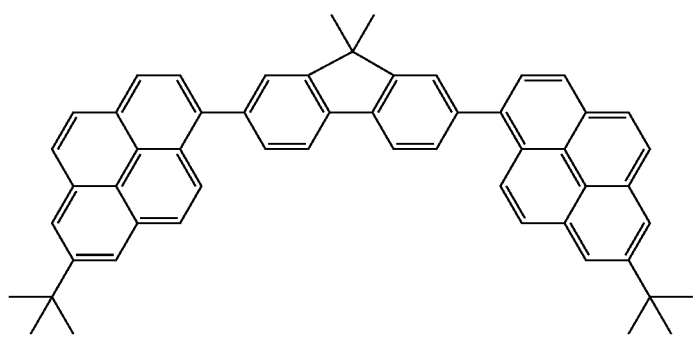
H8
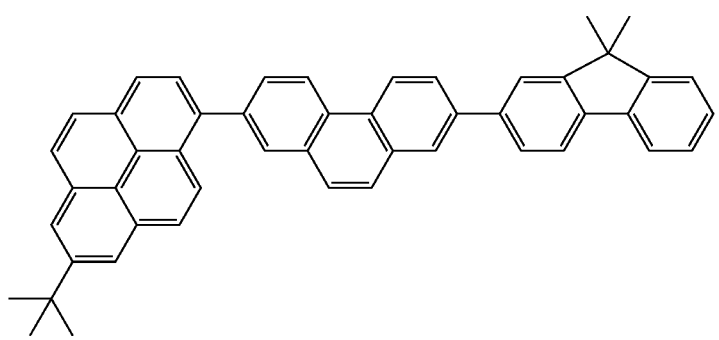
H9
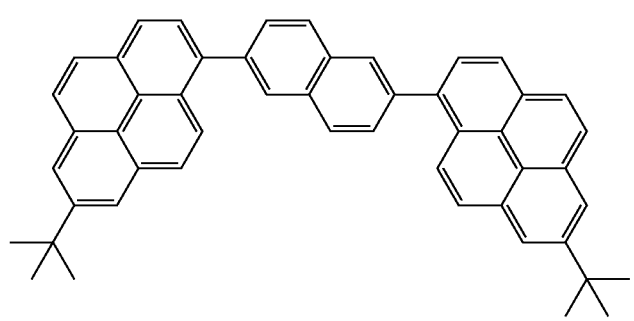
H10
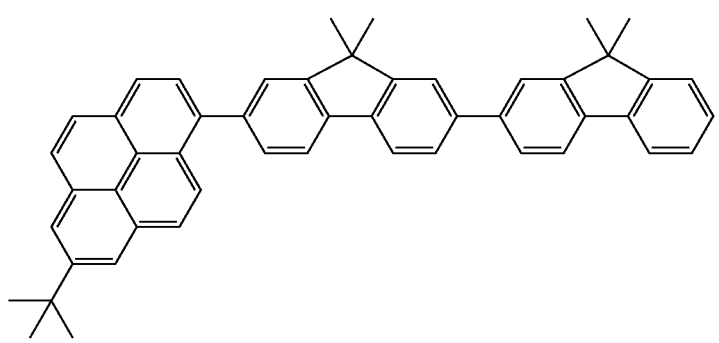
H11

TABLE 3-continued
| | |
|---|---|
| 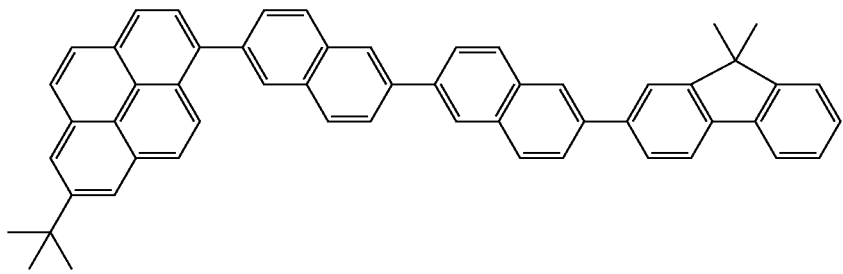 | H12 |
| 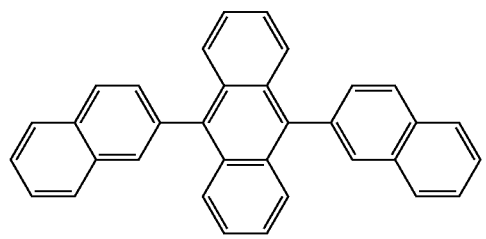 | H13 |
| 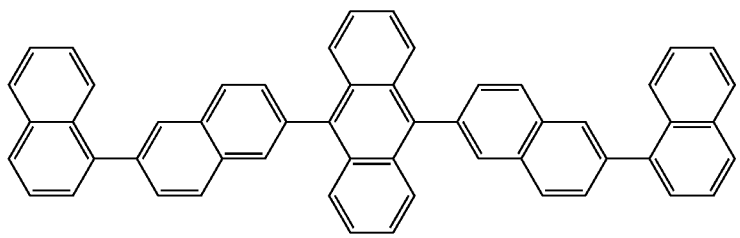 | H14 |
| 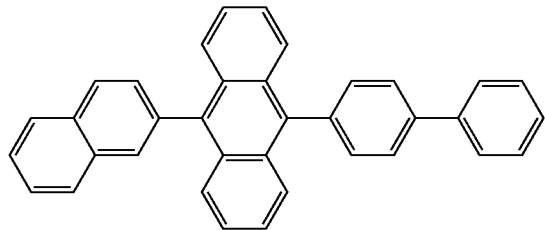 | H15 |
| 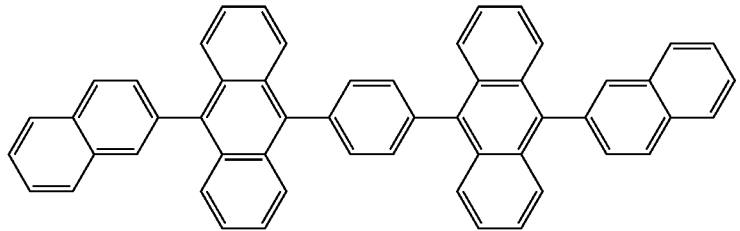 | H16 |
| 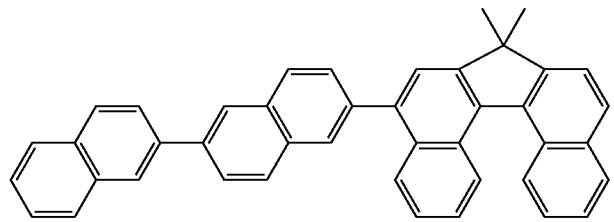 | H17 |

TABLE 3-continued
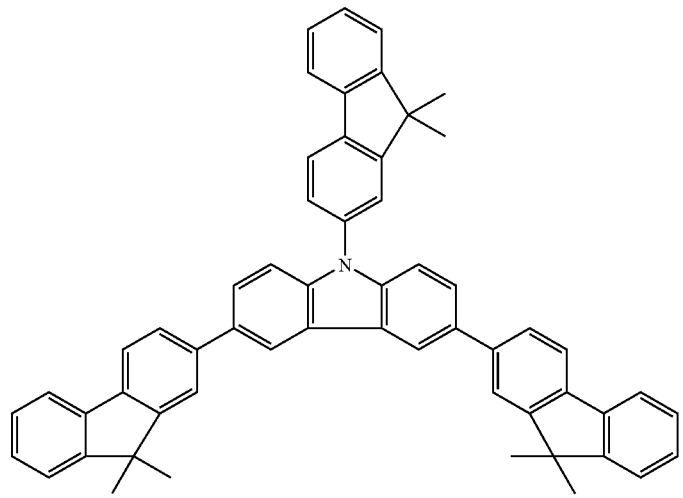
H18
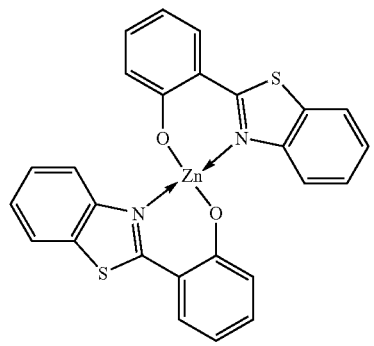
H19
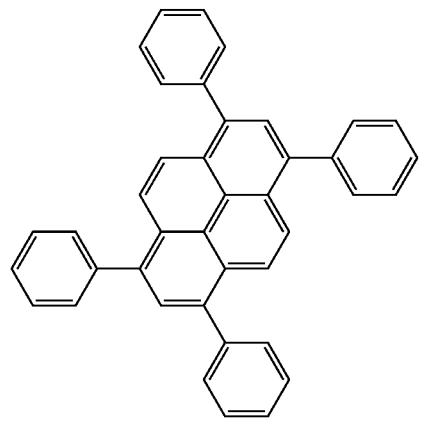
H20
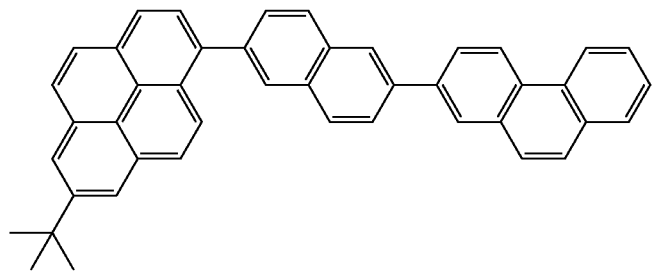
H21

TABLE 3-continued
H22
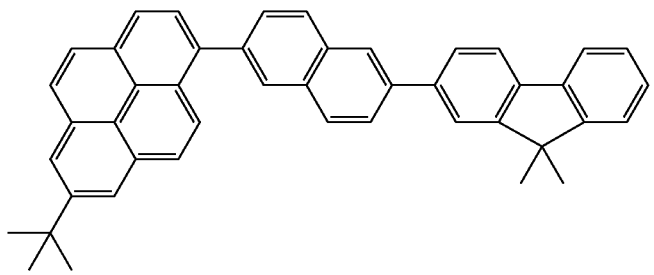
H23
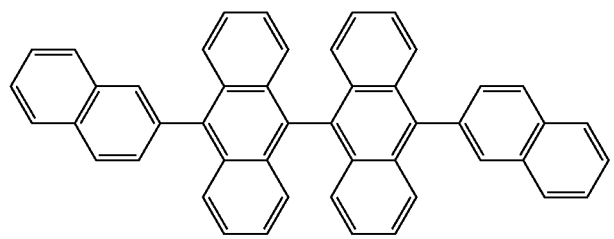
H24
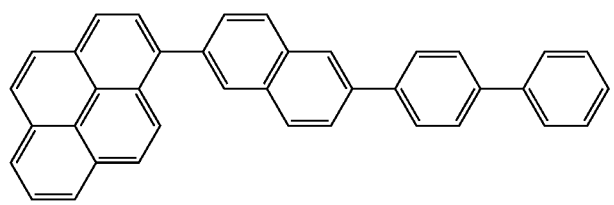
H25
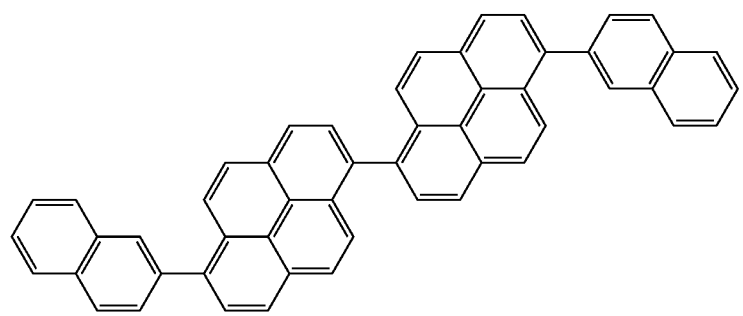
H26
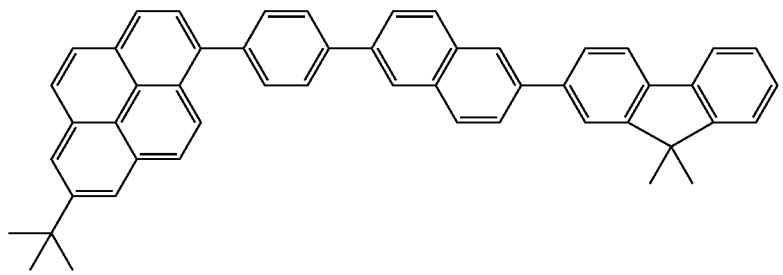

TABLE 3-continued

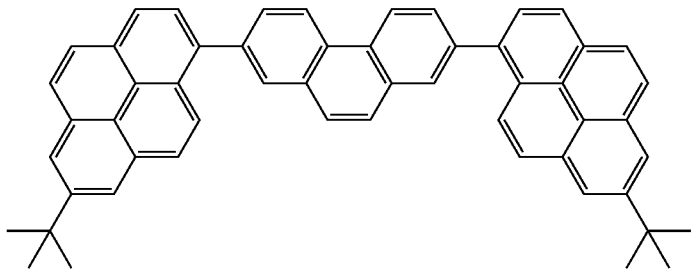

H27

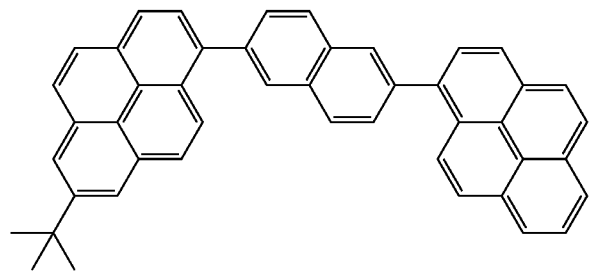

H28

The hole injection/transport material can be adequately selected from those that allow easy injection of electrons from the cathode and transport the injected electrons to the emission layer. A material is selected by considering the balance with the hole mobility of the hole injection/transport material and the like. Examples of the materials having electron injection/transport functions include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

The material for the anode may be a material that has a high work function. Examples thereof include single metals such as gold, platinum, silver, copper, nickel, palladium, cobalt, selenium, vanadium, and tungsten, and their alloys; and metal oxides such as tin oxide, zinc oxide, indium oxide, indium tin oxide (ITO), and zinc indium oxide. Electrically conductive polymers such as polyaniline, polypyrrole, polythiophene, and the like can also be used. These electrode substances may be used alone or in combination. The anode may have a single-layer structure or a multilayer structure.

In contrast, the material for the cathode may be a material that has a low work function. Examples of such a material include alkali metals such as lithium, alkaline earth metals such as calcium, and other single metals such as aluminum, titanium, manganese, silver, lead, and chromium. Alternatively, an alloy combining these single metals may also be used. Examples thereof include magnesium-silver, aluminum-lithium, and aluminum-magnesium. Metal oxides such as indium tin oxide (ITO) may also be used. These electrode substances may be used alone or in combination. The cathode may have a single-layer structure or a multilayer structure.

The substrate used in the organic light-emitting device according to aspects of this invention is not particularly limited. For example, an opaque substrate such as a metal substrate or a ceramic substrate, or a transparent substrate such as a glass substrate, a quartz substrate, or a plastic sheet, may be used. A color filter film, a fluorescence color conversion filter film, a dielectric reflective film, or the like may be formed on the substrate to control the color of emission.

A protective layer or a sealing layer may be provided to the fabricated device in order to prevent the device from contacting oxygen, moisture, and the like. Examples of the protective layer include inorganic material films such as diamond thin films and metal oxide and metal nitride films; polymeric films of fluorocarbon resin, polyethylene, silicone resin, and polystyrene resin; and films of photocurable resin. The device may be covered with glass, a gas-impermeable film, a metal, or the like and packaged with an adequate sealing resin.

In the organic light-emitting device according to aspects of this invention, a layer containing the organic compound according to aspects of this invention and layers containing other organic compounds are formed by the following methods. In general, thin films are formed by vacuum vapor deposition, ionization deposition, sputtering, plasma-enhanced deposition, and various existing coating techniques (e.g., spin-coating, dipping, casting, a Langmuir-Blodgett technique, and ink-jet) that involve dissolving the compounds in adequate solvents. When layers are formed by vacuum vapor deposition or a solution coating technique, crystallization and other unfavorable phenomena rarely occur and stability with time is excellent. When a coating technique is used to form films, an adequate binder resin may be used in combination.

Examples of the binder resin include, but are not limited to, polyvinyl carbazole resin, polycarbonate resin, polyester resin, ABS resin, acryl resin, polyimide resin, phenol resin, epoxy resin, silicone resin, and urea resin. These binder resins may be used alone as a homopolymer or in combination as a copolymer. If needed, existing additives such as a plasticizer, an antioxidant, and an UV absorber may be used in combination.

The organic light-emitting device according to aspects of the present invention can be applied to products that require energy saving and high luminance. Examples of the application include light sources of display apparatuses, lighting apparatuses, and printers, and backlights for liquid crystal display apparatuses.

When the organic light-emitting device is applied to a display apparatus, a high-visibility, light-weight, energy-saving flat panel display can be made. The display apparatus can be used as image-display apparatuses for personal computers, televisions, and advertising media. The display apparatus may be used in a display unit of an image-capturing apparatuses such as digital still cameras and digital video cameras.

Alternatively, the display apparatus may be used in an operation display unit of an electrophotographic image-forming apparatus, e.g., a laser beam printer or a copier.

The organic light-emitting device may be used as a light source for exposing a latent image on a photosensitive member of an electrophotographic image-forming apparatus, e.g., a laser beam printer or a copier. A plurality of organic light-emitting devices that can be addressed independently may be arranged into an array (e.g., lines) and desired exposure may be conducted on a photosensitive drum to form a latent image. Since the organic light-emitting devices according to aspects of this invention are used, the space which has been previously required for placing polygon mirrors, various optical lenses, and the like can be saved.

When the device is applied to lighting apparatuses and backlights, aspects of the present invention can achieve an energy conservation effect. The organic light-emitting device according to aspects of the present invention can also be used as flat surface source.

Alternatively, a color filter film, a fluorescence color conversion filter film, a dielectric reflective film, and other associated components may be formed on the substrate supporting the organic light-emitting device according to aspects of this invention to control the color of emission. A thin film transistor (TFT) may be formed on the substrate and be connected to the organic light-emitting device to control ON and OFF of the emission. A plurality of organic light-emitting devices may be arranged into a matrix, i.e., arranged in an in-plane direction, so that they can be used as a lighting apparatus.

Next, a display apparatus that uses the organic light-emitting device according to aspects of the present invention is described in detail. The display apparatus includes the organic light-emitting device according to aspects of the present invention and a unit configured to supply electrical signals to the organic light-emitting device. The display apparatus according to aspects of the present invention is described in detail below by taking an active matrix system as an example with reference to the drawings.

FIG. 1 is a schematic diagram illustrating an example of configuration of a display apparatus according to one embodiment. The display apparatus includes the organic light-emitting device according to aspects of the present invention and a unit configured to supply electrical signals to the organic light-emitting device according to aspects of the present invention.

Figure 2:
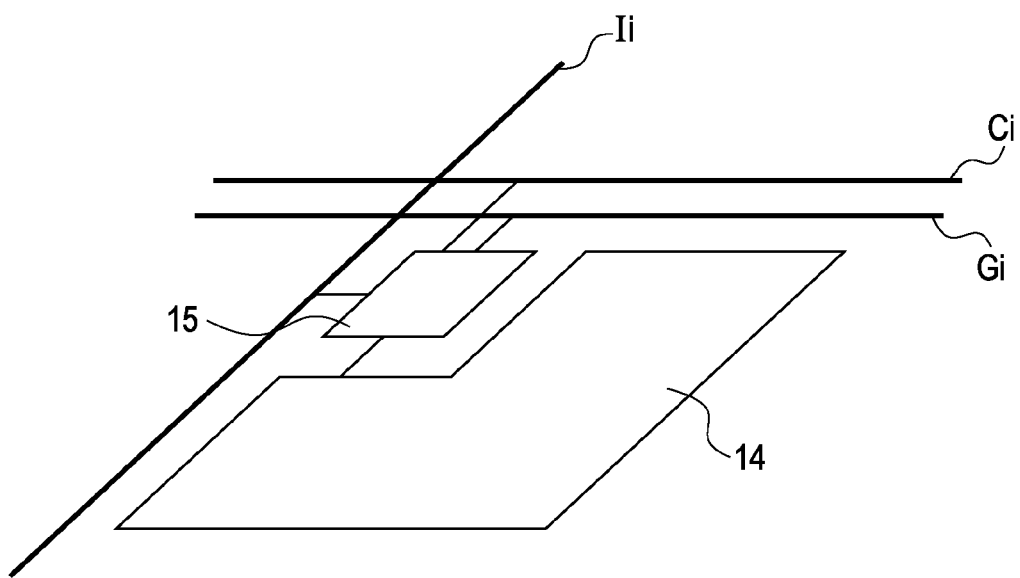
FIG. 2 is a schematic diagram illustrating a pixel circuit connected to a pixel, and signal and electrical current supply lines connected to the pixel circuit.

FIG. 2 is a schematic diagram showing a pixel circuit connected to a pixel, and signal and electrical current supply lines connected to the pixel circuit.

The unit configured to supply electrical signals to the organic light-emitting device according to aspects of the present invention includes a scan signal driver 11, a data signal driver 12, and an electrical current supply source 13 in FIG. 1 and a pixel circuit 15 in FIG. 2.

A display apparatus 1 shown in FIG. 1 includes the scan signal driver 11, the data signal driver 12, and the electrical current supply source 13 which are respectively connected to gate selection lines G, data signal lines I, and electrical current supply lines C. Pixel circuits 15 are arranged at intersections of the gate selection lines G and the data signal lines I, as shown in FIG. 2. One pixel 14 constituted by the organic light-emitting device according to aspects of the present invention is provided for each corresponding pixel circuit 15.

In other words, the pixel 14 is an organic light-emitting device. In the drawing, the organic light-emitting device is illustrated as the emission point. Upper electrodes of the organic light-emitting devices may be formed as a common upper electrode for all of the organic light-emitting devices. Of course, the upper electrodes of the respective organic light-emitting devices may be formed separately.

The scan signal driver 11 sequentially selects gate selection lines G1, G2, G3, . . . and Gn, in synchronization with which image signals are applied to the pixel circuits 15 via one of data signal lines I1, I2, I3, . . . and In from the data signal driver 12.

Figure 3:
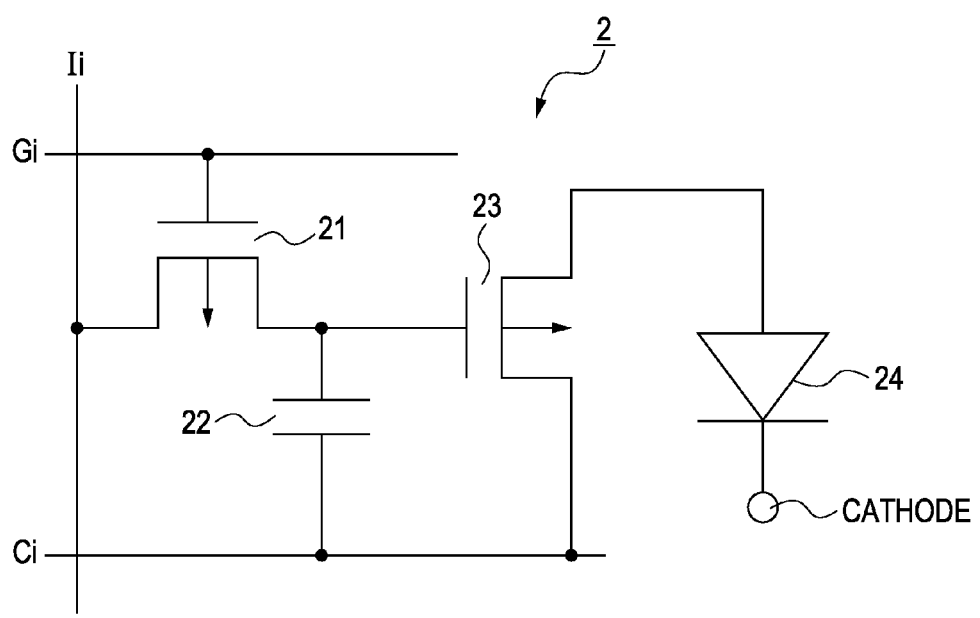
FIG. 3 is a diagram showing the pixel circuit.

Next, operation of a pixel is described. FIG. 3 is a circuit diagram showing a circuit configuring one pixel in the display apparatus 1 shown in FIG. 1. In FIG. 3, a second thin film transistor (TFT) 23 controls the electrical current for causing an organic light-emitting device 24 to emit light. In a pixel circuit 2 in FIG. 3, when a selection signal is applied to a gate selection line G1, the first TFT 21 is turned ON, an image signal Ii is supplied to a capacitor 22, and a gate voltage of the second TFT 23 is thereby determined. An electrical current is supplied to the organic light-emitting device 24 from an electrical current supply line Ci according to the gate voltage of the second TFT 23. Here, the gate potential of the second TFT 23 is retained in the capacitor 22 until the first TFT 21 is scanned and selected next. Accordingly, the electric current keeps flowing in the organic light-emitting device 24 until the next time scanning is performed. As a result, the organic light-emitting device 24 keeps emitting light during one frame period.

Although not shown in the drawings, the organic light-emitting device according to aspects of the present invention can be used in a voltage-write display apparatus in which the voltage between the electrodes of the organic light-emitting device 24 is controlled by a thin film transistor.

Figure 4:
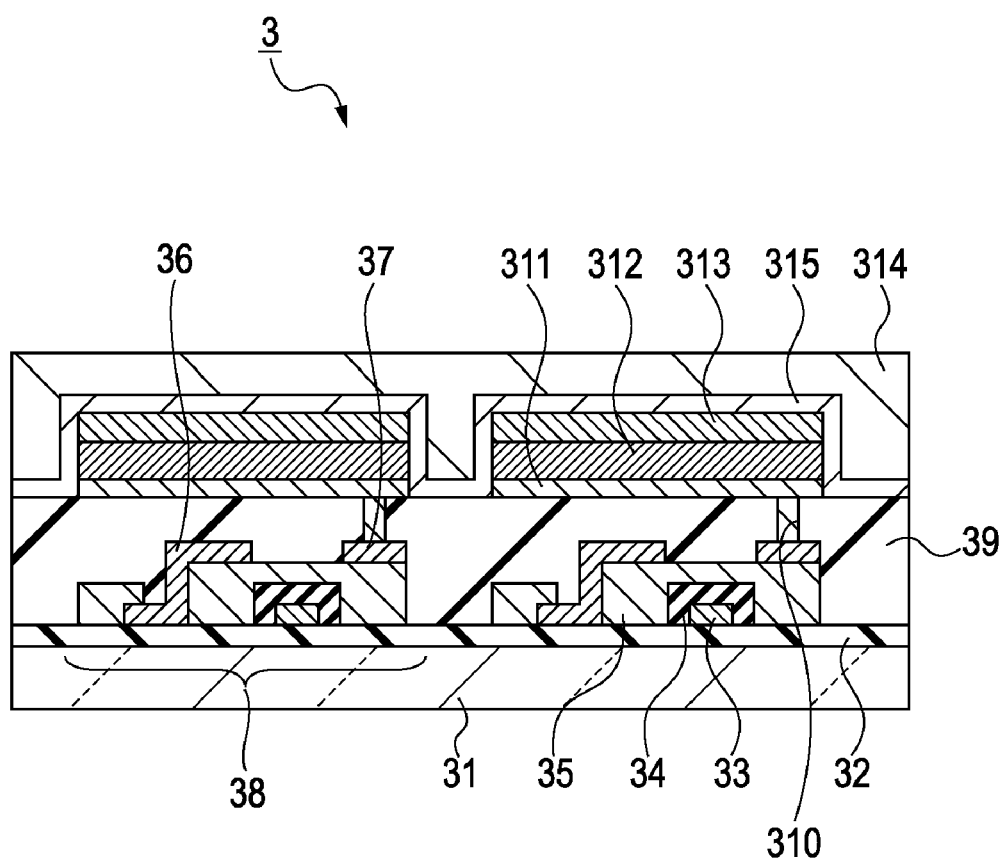
FIG. 4 is a schematic cross-sectional view showing an organic light-emitting device and a thin film transistor underneath.

FIG. 4 is a schematic view showing one example of a cross-sectional structure of a TFT substrate used in the display apparatus shown in FIG. 1. The detailed structure is described below by taking a method for making the TFT substrate as an example.

In making a display apparatus 3 shown in FIG. 4, first, a moisture-proof film 32 for protecting components (TFT or organic layer) formed thereon is formed on a substrate 31 composed of glass or the like by coating. Silicon oxide or a complex of silicon oxide and silicon nitride is used to form the moisture-proof film 32. Next, a metal film of Cr or the like is formed by sputtering and patterned into a particular circuit shape to form a gate electrode 33.

A film of silicon oxide or the like is formed by plasma-enhanced CVD or catalytic chemical vapor deposition (cat-CVD) and patterned to form a gate insulating film 34. A silicon film is formed by plasma-enhanced CVD or the like (annealing at a temperature of 290° C. or more if necessary) and patterned according to a circuit shape to form a semiconductor layer 35.

A drain electrode 36 and a source electrode 37 are formed on the semiconductor layer 35 to form a TFT element 38. As a result, a circuit as shown in FIG. 3 is formed. Next, an insulating film 39 is formed on the TFT element 38. A contact hole (through hole) 310 is formed to connect a metal anode 311 for the organic light-emitting device to the source electrode 37.

A multilayer or single-layer organic layer 312 and a cathode 313 are sequentially layered on the anode 311. As a result, the display apparatus 3 is obtained. A first protective layer 314 and a second protective layer 315 may be provided to prevent deterioration of the organic light-emitting device. When the display panel containing the organic compound according to aspects of the present invention is driven, high-quality images can be displayed stably over a long time.

Note that the switching element of the display apparatus described above is not particularly limited, and the display apparatus can be applied even with a single crystal silicon substrate, a MIM device, an a-Si device, or the like.

An organic light-emitting display panel can be obtained by sequentially layering a single-layer or multilayer organic emission layer and a cathode layer on the ITO electrode. When the display panel containing the organic compound according to aspects of the present invention is driven, high-quality images can be displayed stably over a long time.

As for the direction in which the light is output from the device, either a bottom-emission structure (light is output from the substrate side) or a top-emission structure (light is output from the side opposite the substrate) is applicable.

EXAMPLES

Aspects of the present invention will now be described in further detail by using non-limiting examples.

Example 1

Synthesis of Example Compound A1

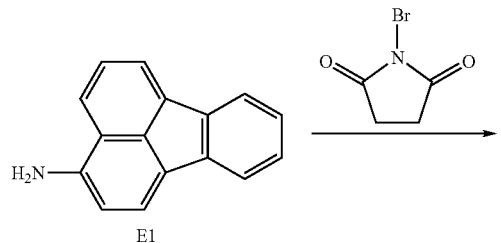

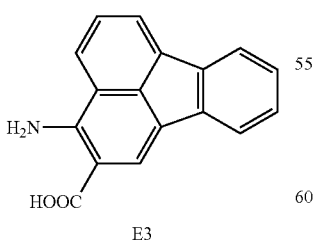

In 300 ml of dimethylformamide, 10.5 g (48 mmol) of fluoranthene-3-amine (E1) was mixed at 0° C., 8.2 g (48 mmol) of N-bromosuccimide was added thereto, and the resulting mixture was returned to room temperature and stirred for 8 hours. The mixture was discharged into water, precipitates were filtered, and recrystallization was conducted in ethanol. Crystals are filtered, washed with heptane, and dried. As a result, 29 g (yield: 60%) of dark brown solid E2 was obtained. In a 500 ml round-bottomed flask, 10 g (34 mmol) E2 was placed and the system was purged with argon. In an argon atmosphere, 150 ml of methoxycyclopentane was added thereto and the resulting mixture was cooled to −75° C. Thereto, 64 ml of a 1.6 M n-butyl lithium solution was added dropwise. Upon completion of the dropwise addition, the mixture was returned to room temperature and stirred for 1 hour. The mixture was cooled again to −75° C. and 15 g of finely crushed dry ice was added to the mixture. The mixture was gradually returned to room temperature. After the mixture was returned to room temperature, it is stirred for 8 hours. The reaction was then terminated by adding 1 M hydrochloric acid. The mixture was extracted with ethyl acetate and the organic layer was condensed to obtain a brown liquid. After the brown liquid had been purified by column chromatography (ethyl acetate/heptane=1:3), recrystallization was conducted with chloroform/methanol to obtain 2.5 g (yield: 28%) of E3 in form of lime green crystals.

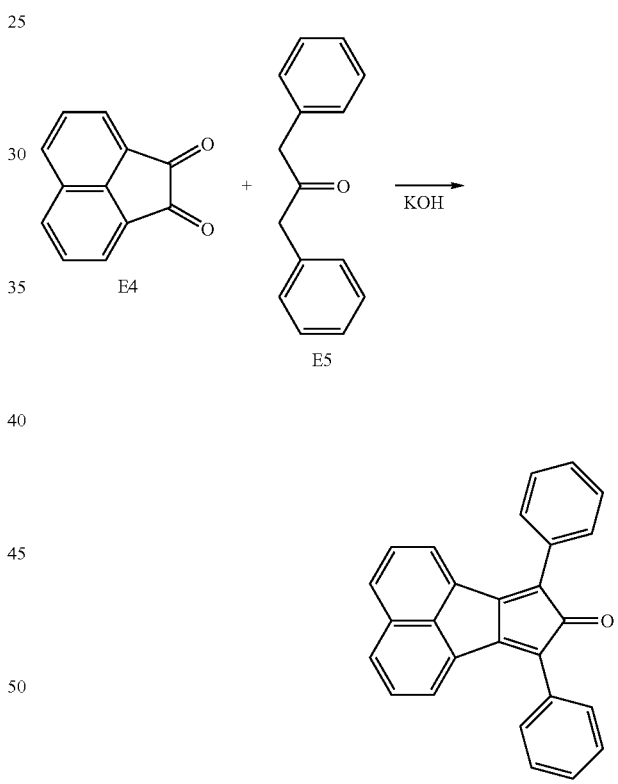

To 200 ml of ethanol, 9.1 g (50 mmol) E4 and 10.5 g (50 mmol) E5 were added, and the resulting mixture was heated to 60° C. To the resulting mixture, 20 ml of a 5 M aqueous sodium hydroxide solution was added dropwise. Upon completion of the dropwise addition, the mixture was heated to 80° C., stirred for 2 hours, and cooled. Precipitates were filtered, washed with water and ethanol, and vacuum-dried under heating at 80° C. As a result, 16 g (yield: 90%) of dark green solid E6 was obtained.

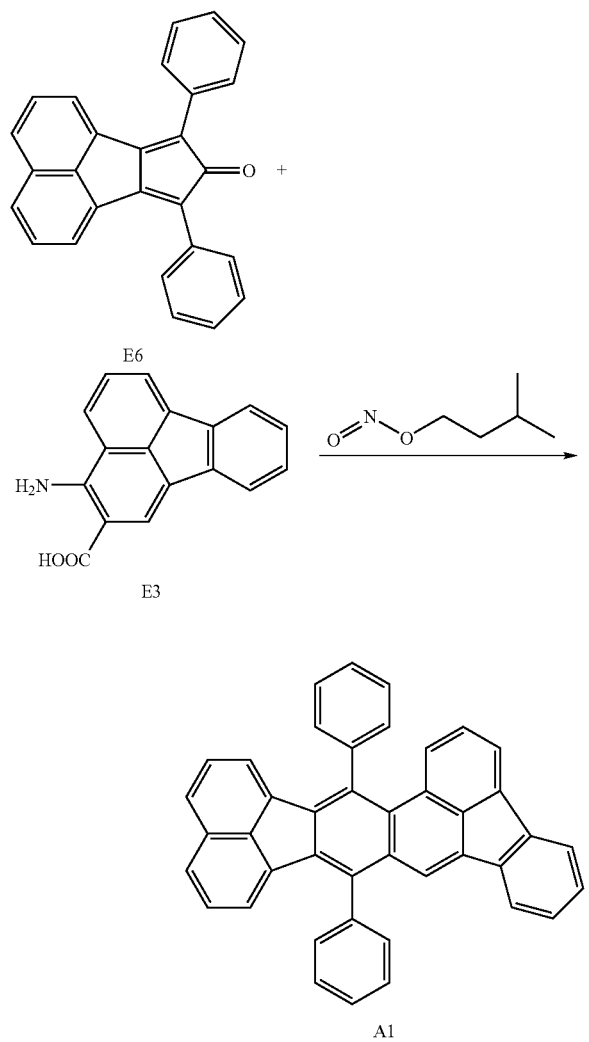

Next, into 50 ml of toluene, 1.8 g (5 mmol) E6 and 1.57 g (6 mmol) E3 were added, and the resulting mixture was heated to 80° C. Then 0.82 g (7 mmol) of isoamyl nitrite was slowly added dropwise, and the resulting mixture was stirred for 3 hours at 110° C. After cooling, the mixture was washed twice with 100 ml of water each time. The organic layer was washed with saturated saline and dried with magnesium sulfate. The resulting solution was filtered and the filtrate was concentrated to obtain a brown liquid. After the brown liquid had been purified by column chromatography (toluene/heptane=1:1), recrystallization was conducted with chloroform/methanol to obtain 2.11 g (yield 80%) of A1 in form of yellow crystals.

The structure of the compound was confirmed by NMR spectroscopy:

$^1$H NMR (CDCl$_3$, 500 MHz) σ (ppm): 8.19 (s, 1H), 7.88-7.64 (m, 14H), 7.37-7.28 (m, 7H), 6.54 (d, 1H, J=7.0 Hz), 6.30 (d, 1H, J=7.5 Hz).

The emission spectrum of a 1×10$^{-5}$ mol/l toluene solution of Example Compound A1 was measured with F-4500 produced by Hitachi Ltd., and photoluminescence was measured at a 350 nm excitation wavelength. The spectrum had the maximum intensity at 440 nm.

Example 2

Synthesis of Example Compound A7

The same reactions and purification were conducted as in Example 1 except that the organic compound was changed from E5 to E7:

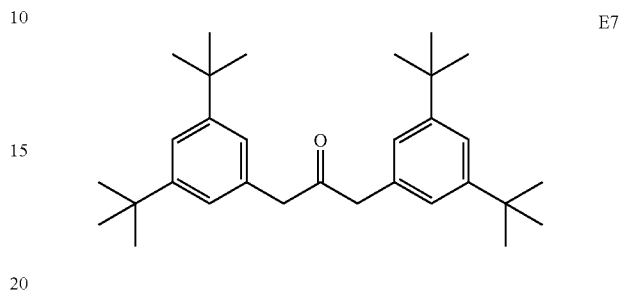

The structure of the compound was confirmed by NMR spectroscopy:

$^1$H NMR (CDCl$_3$, 500 MHz) σ (ppm): 8.32 (s, 1H), 7.88-7.81 (m, 7H), 7.76-7.71 (m, 4H), 7.37-7.28 (m, 6H), 6.54 (d, 1H, J=7.5 Hz), 6.30 (d, 1H, J=7.5 Hz), 1.45 (s, 18H), 1.41 (s, 18H).

The emission spectrum of a 1×10$^{-5}$ mol/l toluene solution of Example Compound A7 was measured with F-4500 produced by Hitachi Ltd., and photoluminescence was measured at a 350 nm excitation wavelength. The spectrum had the maximum intensity at 444 nm.

Example 3

Synthesis of Example Compound A12

The same reactions and purification were conducted as in Example 1 except that the organic compound was changed from E5 to E8:

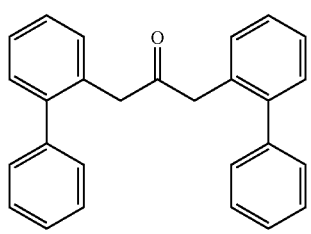

The emission spectrum of a 1×10$^{-5}$ mol/l toluene solution of Example Compound A12 was measured with F-4500 produced by Hitachi Ltd., and photoluminescence was measured at a 350 nm excitation wavelength. The spectrum had the maximum intensity at 443 nm.

Examples 4 to 22

In Examples 4 to 22, multilayer organic light-emitting devices of the fifth example (anode/hole injection layer/hole transport layer/emission layer/hole- and exciton-blocking layer/electron transport layer/cathode) were prepared. An ITO film 100 nm in thickness was formed on a glass substrate by patterning. The following organic layers and electrode layers were continuously formed on the ITO substrate by resistance heating vapor deposition in a vacuum chamber at $10^{-5}$ Pa so that the area of the electrodes facing each other was 3 mm$^2$.

Hole transport layer (30 nm): G-1
Emission layer (30 nm), Host: G-2, Guest: Example Compound (weight ratio: 5%)
Hole/exciton-blocking layer (10 nm): G-3
Electron transport layer (30 nm): G-4
Metal electrode layer 1 (1 nm): LiF
Metal electrode layer 2 (100 nm): Al

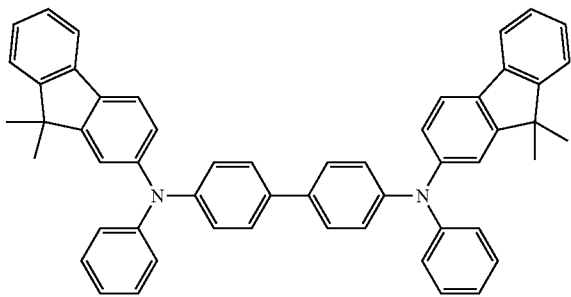

G-1

G-3

G-4

The current-voltage characteristic of each EL device was measured with a pA meter 4140B produced by Hewlett-Packard and the luminance of emission was measured with BM7 produced by Topcon Corporation. The emission efficiency and the voltage observed in Examples 4 to 22 are shown in Table 4 below.

TABLE 4

| | Guest | G-2 | Emission efficiency (cd/A) | Voltage (V) |
|---|---|---|---|---|
| Example 4 | A1 | H9 | 6.2 | 4.3 |
| Example 5 | A1 | H10 | 5.8 | 4.6 |
| Example 6 | A1 | H22 | 6.1 | 4.3 |
| Example 7 | A1 | H23 | 4.8 | 5.0 |
| Example 8 | A6 | H11 | 5.3 | 4.9 |
| Example 9 | A7 | H2 | 4.4 | 5.1 |
| Example 10 | A7 | H26 | 6.4 | 4.4 |
| Example 11 | A9 | H5 | 5.5 | 4.8 |
| Example 12 | A9 | H23 | 4.9 | 5.2 |
| Example 13 | A12 | H8 | 6.0 | 4.4 |
| Example 14 | A12 | H9 | 5.6 | 4.5 |
| Example 15 | A13 | H1 | 5.1 | 5.0 |
| Example 16 | A14 | H21 | 4.8 | 5.1 |
| Example 17 | A16 | H8 | 5.5 | 4.7 |
| Example 18 | A17 | H28 | 3.9 | 5.5 |
| Example 19 | A24 | H18 | 4.2 | 5.3 |

TABLE 4-continued

| | Guest | G-2 | Emission efficiency (cd/A) | Voltage (V) |
|---|---|---|---|---|
| Example 20 | B11 | H4 | 5.0 | 5.1 |
| Example 21 | C1 | H19 | 4.9 | 5.0 |
| Example 22 | C14 | H10 | 4.6 | 5.2 |

Examples 23 to 27

In Examples 23 to 27, multilayer organic light-emitting devices having a structure including an anode, a hole injection layer, a hole transport layer, an emission layer, an electron transport layer, an electron injection layer, and a cathode sequentially stacked on a substrate were prepared.

An organic light-emitting device having a resonant structure was made by the following process.

An aluminum alloy (AlNd) was deposited on a glass substrate serving as a supporting member by sputtering so as to make a 100 nm-thick film as a reflexive anode. Then ITO was sputter-deposited thereon to form a 80-nm thick film as a transparent anode. An acrylic device isolation film having a thickness of 1.5 μm was formed around the anode, and an opening having a radius of 3 mm was formed. The resulting product was ultrasonically washed with acetone and then with isopropyl alcohol (IPA), boiled and washed in IPA, and dried. The substrate surface was then washed with UV/ozone.

Organic layers described below were continuously vacuum-deposited by resistance heating in a vacuum chamber at $10^{-5}$ Pa. IZO was sputter-deposited to form a 30 nm-thick transparent electrode that served as the cathode. The resulting layers were placed in a nitrogen atmosphere and sealed.

The organic light-emitting device included the following layers:

Hole injection layer (95 nm): G-11
Hole transport layer (10 nm): G-12
Emission layer (35 nm), Host: G-13, Guest: Example Compound (weight ratio: 2%)
Electron transport layer (10 nm): G-14
Electron injection layer (70 nm): G-15 (weight ratio: 80%), Li (weight ratio: 20%)

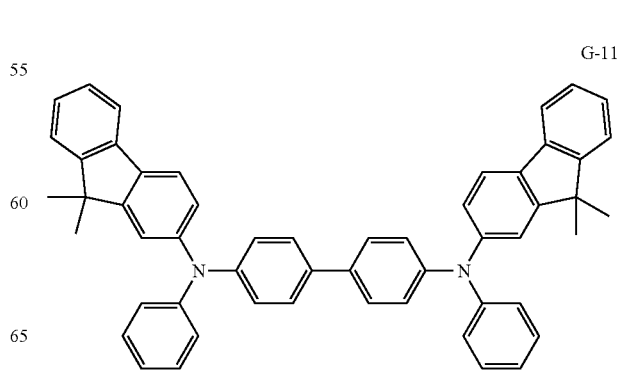

G-11

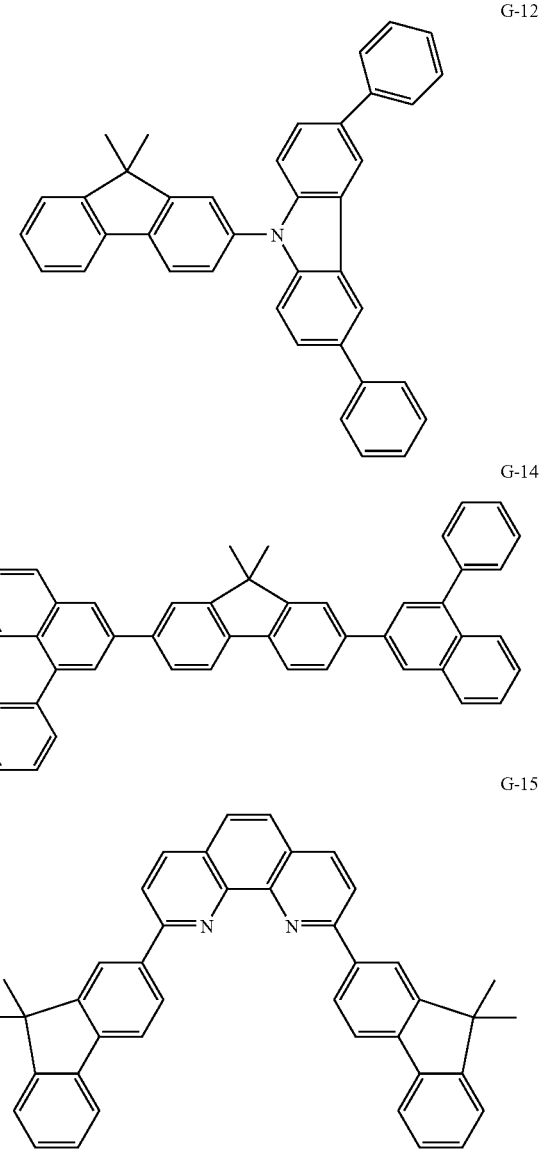

The current-voltage characteristic of each EL device was measured with a pA meter 4140B produced by Hewlett-Packard and the luminance of emission was measured with BM7 produced by Topcon Corporation. The emission efficiency and the voltage observed in Examples 23 to 27 are shown in Table 5 below.

TABLE 5

|  | Guest | G-13 | Emission efficiency (cd/A) | Voltage (V) |
|---|---|---|---|---|
| Example 23 | A1 | H7 | 3.2 | 4.2 |
| Example 24 | A7 | H22 | 2.9 | 4.3 |
| Example 25 | A12 | H8 | 3.1 | 4.1 |
| Example 26 | A14 | H10 | 3.4 | 4.1 |
| Example 27 | A27 | H8 | 3.0 | 4.0 |

Results and Studies

The organic compounds according to aspects of the present invention are novel compounds that achieve high quantum yields and emission suitable for blue emission. When the organic compounds are used in organic light-emitting devices, the organic light-emitting devices can exhibit good emission characteristics. Thus, the examples show that a novel organic compound may be provided that is suitable for use in a blue light-emitting device, and an organic light-emitting device including this novel organic compound may also be provided. The novel organic compound may be capable of realizing excellent color purity and highly efficient emission. An organic light-emitting device including such a novel organic compound may also be capable of realizing highly efficient high-luminance emission.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-105355 filed Apr. 23, 2009, which is hereby incorporated by reference herein in its entirety.

What is claimed is:

1. An organic compound comprising:
   an acenaphtho[1,2-k]benzo[e]acephenanthrene derivative represented by general formula (1):

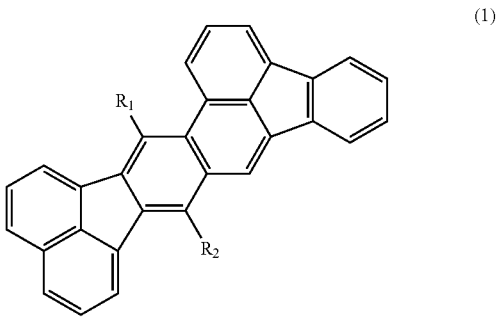

(1)

where $R_1$ and $R_2$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

2. The organic compound according to claim 1, wherein $R_1$ and $R_2$ each independently represent a substituted or unsubstituted aryl group.

3. An organic light-emitting device comprising:
   a cathode;
   an anode; and
   an organic compound layer interposed between the anode and the cathode, the organic compound layer comprising the organic compound according to claim 1.

4. The organic light-emitting device according to claim 3, wherein the organic compound layer is an emission layer.

5. An image display apparatus comprising:
   a plurality of pixels each including the organic light-emitting device according to claim 3; and
   a unit configured to supply an electrical signal to the organic light-emitting device.

* * * * *